(12) United States Patent
Gao et al.

(10) Patent No.: US 9,623,112 B2
(45) Date of Patent: Apr. 18, 2017

(54) DUALLY DERIVATIZED CHITOSAN NANOPARTICLES AND METHODS OF MAKING AND USING THE SAME

(71) Applicant: enGene, Inc., Vancouver (CA)

(72) Inventors: Jun Gao, Coquitlam (CA); Eric Hsu, Vancouver (CA); Anthony Cheung, Vancouver (CA)

(73) Assignee: ENGENE, INC., Montreal, QC ( * ) Notice: Subject to any disclaimer, the term of this patent is extended or adjusted under 35 U.S.C. 154(b) by 40 days.

(21) Appl. No.: 14/386,321

(22) PCT Filed: Mar. 15, 2013

(86) PCT No.: PCT/CA2013/050218
§ 371 (c)(1),
(2) Date: Sep. 18, 2014

(87) PCT Pub. No.: WO2013/138930
PCT Pub. Date: Sep. 26, 2013

(65) Prior Publication Data
US 2015/0051265 A1    Feb. 19, 2015

Related U.S. Application Data

(60) Provisional application No. 61/613,885, filed on Mar. 21, 2012.

(51) Int. Cl.
| | | |
|---|---|---|
| A61K 47/36 | (2006.01) | |
| C12N 15/87 | (2006.01) | |
| A61K 47/48 | (2006.01) | |
| C07H 5/06 | (2006.01) | |
| C07H 13/04 | (2006.01) | |
| C08B 37/08 | (2006.01) | |
| C12N 15/11 | (2006.01) | |
| C08L 5/08 | (2006.01) | |
| A61K 9/51 | (2006.01) | |

(52) U.S. Cl.
CPC .... *A61K 47/4823* (2013.01); *A61K 47/48923* (2013.01); *C07H 5/06* (2013.01); *C07H 13/04* (2013.01); *C08B 37/003* (2013.01); *C08L 5/08* (2013.01); *C12N 15/111* (2013.01); *C12N 15/87* (2013.01); *A61K 9/5161* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 8,431,543 B2 | 4/2013 | Park et al. |
| 2007/0281904 A1 | 12/2007 | Baker et al. |
| 2012/0295355 A1 | 11/2012 | Baker et al. |

FOREIGN PATENT DOCUMENTS

| | | | |
|---|---|---|---|
| KR | WO 2008/082282 | * | 7/2008 |
| WO | WO 2008/082282 A1 | | 1/2008 |
| WO | WO 2010/088565 A1 | | 8/2010 |
| WO | WO 2012/105685 A1 | | 8/2012 |
| WO | WO 2013/138930 A1 | | 9/2013 |

OTHER PUBLICATIONS

Gao, D. et al., "Arginine-chitosan/DNA self-assemble nanoparticles for gene delivery: In vitro characteristics and transfection efficiency," International Journal of Pharmaceutics, vol. 359, pp. 241-246, (2008).
Hashimoto, M. et al., "Chitosan," Taira, K. et al. (Eds.), Non-viral Gene Therapy: Gene Design and Delivery, pp. 63-74, (2005).
Mao, S. et al., "Chitosan-based formulations for delivery of DNA and siRNA. Advanced Drug Delivery Reviews," vol. 62, 2010, pp. 12-27, (2009).
Park, J.H. et al. "Synthesis and characterization of sugar bearing chitosan derivatives: aqueous solubility and biodegradability," Biomacromolecules, vol. 4, No. 4, pp. 1087-1091, (2003).
Varma, A.J. et al, "Metal complexation by chitosan derivatives: a review," Carboydrat Polymers, vol. 55, pp. 77-93, (2004).
Zhu, D. et al. "Enhancement of transfection efficiency for Hela cells via incorporating arginine moiety into chitosan." Chinese Science Bulletin, vol. 52, No. 23, pp. 3207-3215, (2007).

* cited by examiner

*Primary Examiner* — Jennifer McDonald
(74) *Attorney, Agent, or Firm* — Todd A. Lorenz

(57) ABSTRACT

Provided herein is chitosan dually derivatized with arginine and gluconic acid; and methods of making and using the same, e.g., for gene delivery in vivo.

26 Claims, 14 Drawing Sheets

FIG. 12

| Test | Accept. Crit. | DD-EG-10 Frozen | DD-EG-10 Lyophilized | DD-EG-10 Lyophilized (after 3Mo) |
|---|---|---|---|---|
| Plasmids | | CMV-hIL-10 | CMV-hIL-10 | CMV-hIL-10 |
| [DNA] | | 900 ug/ml (Batch 192-92) | 900 ug/ml (Batch 192-92) | 900 ug/ml (Batch 192-92) |
| Physicochemical Properties | | | | |
| pH | 5.5-6.5 | 6.0 | 6.0 | 6.0 |
| Size (nm) | <200nm | 96 | 99 | 99 |
| Zeta Potential (mV) | >30 mV | 30 | 29 | 30 |
| PDI | <0.25 | 0.081 | 0.076 | 0.09 |
| Stability @ RT O/N | Size & PDI | 96nm, 0.099 | 100nm, 0.101 | 97nm, 0.100 |
| Purity | | | | |
| None-complex DNA (AGE) | No free DNA | No free DNA | No free DNA | No free DNA |

DUALLY DERIVATIZED CHITOSAN NANOPARTICLES AND METHODS OF MAKING AND USING THE SAME

FIELD OF INVENTION

The present invention generally relates to nanoparticles comprising dually derivatized chitosan, and methods of making and using the same for delivering nucleic acids, e.g., gene transfer, in vivo.

BACKGROUND OF THE INVENTION

Chitosan is a non-toxic cationic copolymer of N-acetyl-D-glucosamine and D-glucosamine. Chitosan can form a complex with nucleic acid and, as a biocompatible and non-toxic polysaccharide, has been used as a DNA delivery vehicle to transfect cells. Much interest has been focused on using chitosan in non-viral delivery of nucleic acid due to the complexities and potential toxicity of the viral envelope.

A number of chitosan/DNA complexes, including complexes between modified chitosan and nucleic acids, have been examined in an attempt to identify compositions well suited for gene transfection. See, e.g., WO2010/088565; WO2008/082282. The complexes have been found to vary in, among other properties, solubility, propensity for aggregation, complex stability, particle size, ability to release DNA, and transfection efficiency.

Provided herein is the surprising discovery that arginine and gluconic acid act synergistically to improve the transfection efficiency of chitosan.

SUMMARY OF INVENTION

Disclosed herein is the unexpected finding that arginine and gluconic acid synergistically increase the transfection efficiency of chitosan nanoparticles, Accordingly provided herein are novel compositions to facilitate the delivery of nucleic acids to cells, tissues, and organs, e.g., in vivo. In particular, provided herein are dually derivatized chitosan based nanoparticles, wherein said nanoparticles optionally further comprise nucleic acid.

In one embodiment, the nanoparticles comprise chitosan that is coupled at least to an amino acid. In a preferred embodiment, the amino acid is positively charged. In a more preferred embodiment, the amino acid is arginine.

In another embodiment, the nanoparticles comprise chitosan that is coupled to an organic acid, preferably to gluconic acid.

In another embodiment, the nanoparticles comprise chitosan that is coupled to both arginine and gluconic acid, see, e.g., Formula I

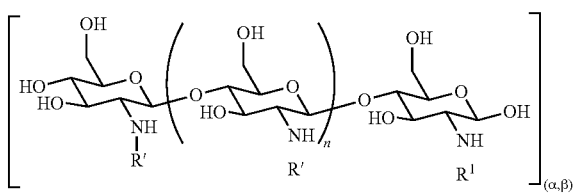

(I)

wherein n is an integer of 1 to 2000,
α is the functionalization degree of arginine,
β is the functionalization degree of gluconic acid; and
each $R^1$ is independently selected from hydrogen, acetyl, Formula (II), and Formula (III).

(II)

(III)

Dually derivatized chitosan as described herein comprise arginine and gluconic acid at varying initial concentration percentages or final functionalization percentage. Initial concentration percentage is used for gluconic acid modified chitosan, which represents the molar ratio of carboxyl group on gluconic acid divided by the total amine groups on chitosan or arginine-modified chitosan, while the final functionalization percentage represent the functionalization degree of final modified chitosan calculated from carbon and nitrogen weight ratio as result of elemental analysis. In one embodiment, chitosan is coupled with gluconic acid at an initial concentration of about 5% to about 60%, e.g., about 8% to about 30%. In another embodiment, preferably about 30%. In another embodiment, chitosan is coupled with arginine at a final concentration of about 10% to about 55%.

In particular, chitosan-nucleic acid polyplexes formed with such dually derivatized chitosan ("DD-chitosan") exhibit a higher transfection efficiency than nucleic acid polyplexes formed with either non-functionalized chitosan or chitosan that is conjugated to either single amino acid residues, amino acid polymers, or gluconic acid residues alone. Other desirable properties conferred by the use of dually functionalized chitosan in polyplexes described herein include an improved ability to penetrate the mucous barrier, enhanced polyplex stability, reduced cellular toxicity and enhanced intracellular release of nucleic acid. Further, in some preferred embodiments, the subject DD-chitosan polyplex compositions can be administered at physiological pH (e.g., systemic administration).

Accordingly, in one aspect, the invention provides DD-chitosan nucleic acid polyplexes. The DD-chitosan nucleic acid polyplexes comprise chitosan that is dually derivatized with arginine and gluconic acid.

In one embodiment, the DD-chitosan nucleic acid polyplex is formed at a pH below the pKa of DD-chitosan.

In one embodiment, the DD-chitosan nucleic acid polyplex is formed at a pH below 7.

In one embodiment, the DD-chitosan nucleic acid polyplex has a combined degree of functionalization with arginine and gluconic acid of 1-60%.

In one embodiment, the DD-chitosan nucleic acid polyplex has a combined degree of functionalization with arginine and gluconic acid of 1-30%.

In one embodiment, the molar ratio of arginine to gluconic acid in the DD-chitosan nucleic acid polyplex is between 100:1 and 1:100.

In one embodiment, the molar ratio of arginine to gluconic acid in the DD-chitosan nucleic acid polyplex is between 50:1 and 1:50.

In one embodiment, the molar ratio of arginine to gluconic acid in the DD-chitosan nucleic acid polyplex is between 10:1 and 1:10.

In one embodiment, the molar ratio of arginine to gluconic acid in the DD-chitosan nucleic acid polyplex is between 5:1 and 1:5.

In one embodiment, the molar ratio of arginine to gluconic acid in the DD-chitosan nucleic acid polyplex is between 2:1 and 1:2.

In preferred embodiments, the molar ratio of arginine to gluconic acid is inversely proportional to the molecular weight of the chitosan, i.e., a smaller molecular weight DD-chitosan requires a higher molar ratio of arginine to chitosan, and vice-verse.

In one embodiment, the nucleic acid of the DD-chitosan nucleic acid polyplex is DNA.

In one embodiment, the nucleic acid of the DD-chitosan nucleic acid polyplex is RNA.

In one embodiment, the nucleic acid of the DD-chitosan nucleic acid polyplex is an artificial nucleic acid. In a preferred embodiment, the artificial nucleic acid is selected from the group consisting of peptide nucleic acid (PNA), phosphorodiamidate morpholino oligo (PMO), locked nucleic acid (LNA), glycol nucleic acid (GNA) and threose nucleic acid (TNA).

In one embodiment, the nucleic acid of the DD-chitosan nucleic acid polyplex is a therapeutic nucleic acid. In one embodiment, the therapeutic nucleic acid is a therapeutic RNA.

In a preferred embodiment, the therapeutic RNA is selected from the group consisting of antisense RNA, siRNA, short hairpin RNA, micro RNA, and enzymatic RNA.

In one embodiment, the therapeutic nucleic acid is DNA.

In one embodiment, the therapeutic nucleic acid comprises a nucleic acid sequence encoding a therapeutic protein.

In one aspect, the invention provides a composition comprising a plurality of DD-chitosan nucleic acid polyplexes.

In one embodiment, the composition has a pH between 3.0-8.0, more preferably between 4.0-7.0, and most preferably between 4.5-6.5.

In one aspect, the invention provides a pharmaceutical composition comprising a DD-chitosan nucleic acid polyplex of the invention. In a preferred embodiment, the DD-chitosan nucleic acid polyplex comprises a therapeutic nucleic acid.

In one aspect, the invention provides methods of treating disease, comprising administering a therapeutically effective amount of a pharmaceutical composition of the invention to a patient.

In one embodiment, the subject pharmaceutical composition is administered at physiological pH.

In one embodiment, the subject pharmaceutical composition is administered systemically.

In one embodiment, the subject pharmaceutical composition is administered locally to a target tissue. In a preferred embodiment, the subject pharmaceutical composition is administered to mucosal tissue. In one embodiment, the mucosal tissue is GI tissue.

In one aspect, the invention provides a vaccine, comprising a DD-chitosan nucleic acid polyplex, wherein the nucleic acid encodes an antigen.

In one aspect, the invention provides methods for vaccinating a patient. The methods comprise administering a vaccine of the invention to a patient.

In one aspect, the invention provides an immunogenic composition, comprising an DD-chitosan nucleic acid polyplex, wherein the nucleic acid encodes an immunogen.

In one aspect, the invention provides methods for initiating or increasing an immune response to a molecule of the interest. The methods comprise administering an immunogenic composition of the invention to a patient, wherein the nucleic acid encodes an epitope of the molecule of interest.

BRIEF DESCRIPTION OF THE DRAWINGS

FIG. 12 shows physicochemical property of lyophilized DD-chitosan-nucleic acid polyplexes following reconstitution with water after 3 months storage at room temperature.

DETAILED DESCRIPTION

Figure 1:
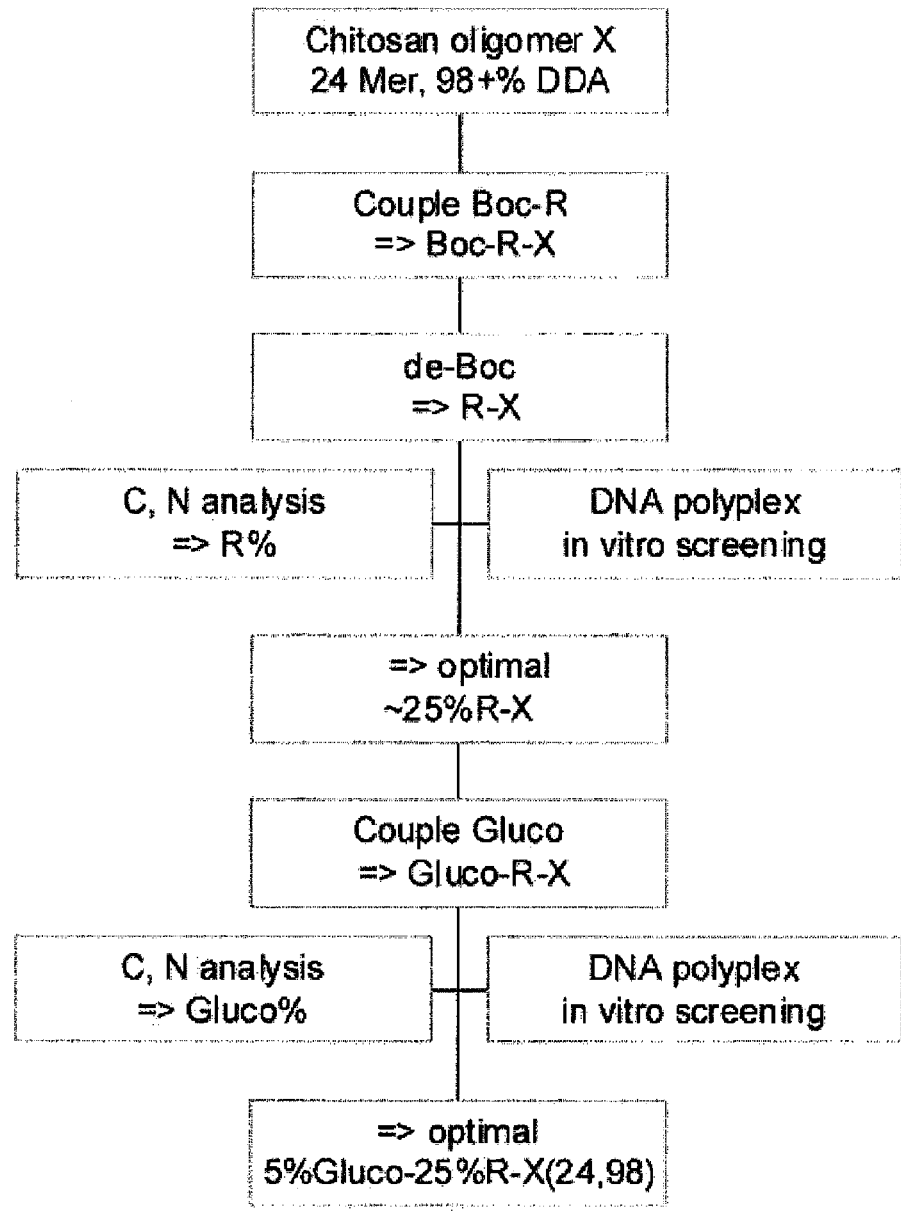
FIG. 1 is a flow diagram of the process of making chitosan dually derivatized with arginine and gluconic acid leading to an optimal combination of functionalization degrees between two coupled components.
Figure 2A:
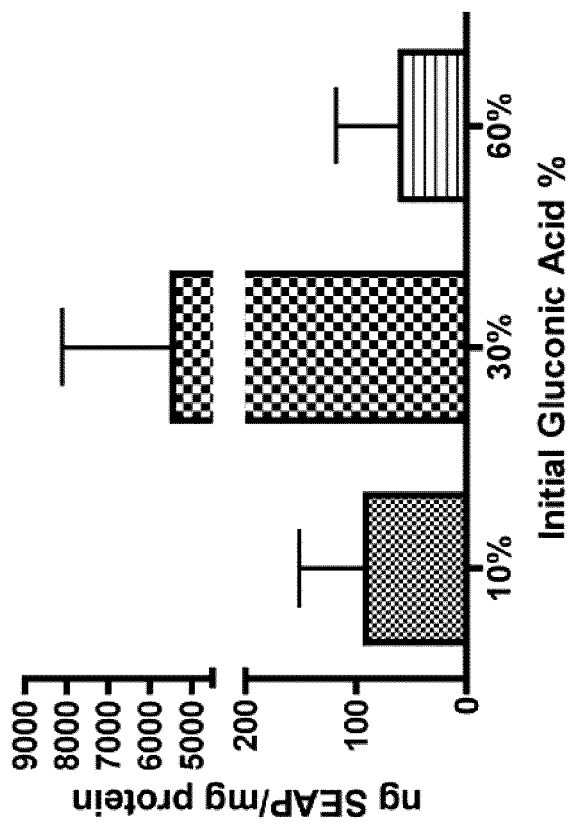
FIG. 2 shows the transfection efficiency (ng SEAP/mg protein; y-axis) of 24mer chitosan coupled with (A) gluconic acid at an initial concentration (x-axis) of 10%, 30%, or 60% or (B) arginine at a final functionalization degree (x-axis) of 9.7%, 12.3%, 26%, or 52%.
Figure 2B:
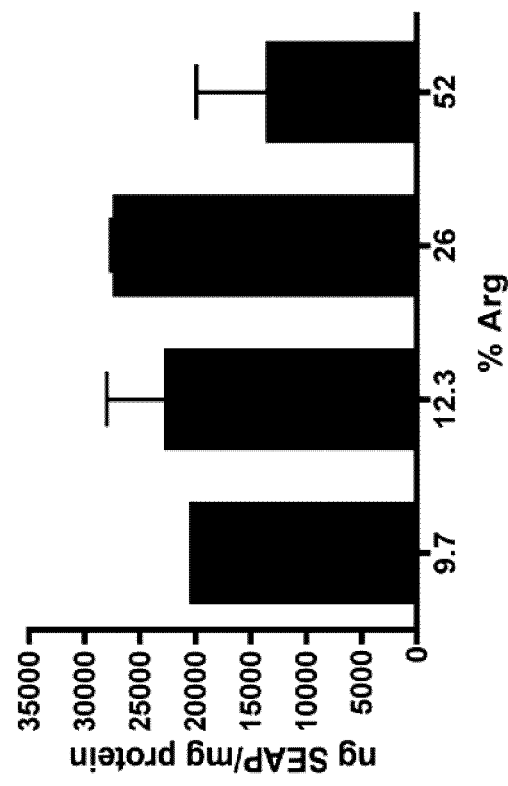

Chitosan is the deacetylated form of chitin, which is a polymer of N-acetylglucosamine that is the main component of the exoskeletons of crustaceans (e.g. shrimp, crab, lobster). Chitosan is formed from chitin by deacetylation, and as such is not a single polymeric molecule, but a class of molecules having different molecular weights and different degrees of deacetylation. The percent deacetylation in commercial chitosans is typically between 50-100%.

The chitosan derivatives described herein are generated by functionalizing the resulting free amino groups with positively charged or neutral moieties, as described herein. The derivatized chitosans described herein have a number of properties which are advantageous for a nucleic acid delivery vehicle including: they effectively bind and complex the negatively charged nucleic acids, they can be formed into nanoparticles of a controllable size, they can be taken up by the cells and they can release the nucleic acids at the appropriate time within the cells.

Chitosans with any degree of deacetylation greater than 50% are used in the present invention, with functionalization between 1% and 50%. (Percent functionalization is determined relative to the number of free amino moieties on the chitosan polymer.) The degrees of deacetylation and functionalization impart a specific charge density to the functionalized chitosan derivative. The resulting charge density affects solubility, nucleic acid binding and subsequent release, and interaction with mammalian cell membranes. Thus, in accordance with the present invention, these properties must be optimized for optimal efficacy. Exemplary chitosan derivatives are described in Baker et al; Ser. No. 11/657,382 filed on Jan. 24, 2007, which is incorporated herein by reference. In one embodiment, the dually derivatized chitosan described herein comprises chitosan having a degree of deacetylation of at least 50%. In one embodiment, the degree of deacetylation is at least 60%, more preferably at least 70%, more preferably at least 80%, more preferably at least 90%, and most preferably at least 95%. In a preferred embodiment, the dually derivatized chitosan described herein comprises chitosan having a degree of deacetylation of at least 98%.

The chitosan derivatives described herein have a range of average molecular weights that are soluble at neutral and physiological pH, and include for the purposes of this invention molecular weights ranging from 3-110 kDa. Embodiments described herein are feature lower average molecular weight of derivatized chitosans (<25 kDa, e.g., from about 5 kDa to about 25 kDa), which can have desirable delivery and transfection properties, and are small in size and have favorable solubilities. A lower average molecular weight derivatized chitosan is generally more soluble than one with a higher molecular weight, the former thus producing a nucleic acid/chitosan complex that will release more easily the nucleic acid and provide increased transfection of cells. Much literature has been devoted to the optimization of all of these parameters for chitosan based delivery systems.

An ordinarily skilled artisan will recognize that chitosan refers to a plurality of molecules having a structure of Formula I, wherein n is any integer, and each $R^1$ is hydrogen. Also, chitosan referred to as having an average molecular weight, e.g., of 3 kD to 110 kD, generally refers to a plurality of chitosan molecules having a weight average molecular weight of, e.g., 3 kD to 110 kD, respectively, wherein each of the chitosan molecules may have different chain lengths (n+2). It is also well-recognized that chitosan referred to as "n-mer chitosan," does not necessarily comprise chitosan molecules of Formula I, wherein each chitosan molecule has a chain length of n+2. Rather, "n-mer chitosan" as used herein refers a plurality of chitosan molecules, each of which may have different chain lengths, wherein the plurality has an average molecule weight substantially similar to or equal to a chitosan molecule having a chain length of n. For example, 24-mer chitosan may comprise a plurality chitosan molecules, each having different chain lengths ranging from, e.g., 7-50, but which has a weight average molecular weight substantially similar or equivalent to a chitosan molecule having a chain length of 24.

The functionalized chitosan derivatives described herein are dually derivatized-chitosan compounds, e.g., chitosan-arginine-gluconic acid compounds. In general, the chitosan-arginine-gluconic acid compounds have the following structure of Formula I

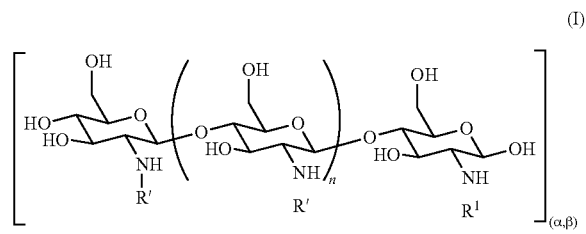

wherein n is an integer of 1 to 2000,

α is the functionalization degree of arginine,

β is the functionalization degree of gluconic acid; and each $R^1$ is independently selected from hydrogen, acetyl, Formula (II), and Formula (III).

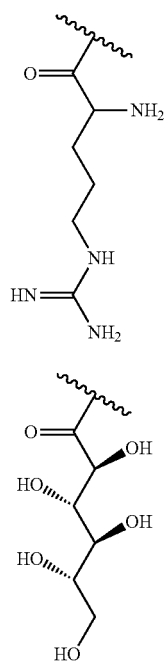

(II)

(III)

A preferred method for conjugating chitosan with arginine or gluconic acid in an aqueous medium, in accordance with the present invention, is described herein, in which Boc-L-arginine (Boc-R) and gluconic acid (Gluco) are used. The method utilizes well-known water soluble 1-Ethyl-3-(3-Dimethylaminopropyl)-carbodiimide (EDC) and N-hydroxysuccinimide (NHS) to catalyze the formation of amide between an amine on the chitosan backbone and a carboxylic acid on Boc-R or gluconic acid.

Generally, chitosan in dilute HCl solution with an adjusted pH for a targeted coupling pH of, e.g., 6.0±0.5 and more preferably 6.0±0.2, is first coupled to either Boc-R or Gluco, purified, and then coupled with the second functional group. For example, if chitosan is first coupled to arginine, the arginine-coupled chitosan (R-chitosan) may be purified and then coupled to gluconic acid. Conversely, if chitosan is first coupled to gluconic acid, the gluconic acid-coupled chitosan (gluco-chitosan) may be purified and then coupled to arginine. Irrespective of the order of coupling, arginine and gluconic acid may be coupled to chitosan using well-known methods.

For example, arginine may be coupled to chitosan or gluco-functionalized chitosan (gluco-chitosan) by adding a mixture of Boc-R and NHS aqueous solution of adjusted pH into chitosan in dilute HCl followed by adding EDC water solution to initiate coupling at room temperature for 24 hours. The concentration of chitosan amine, reaction pH and the molar ratios of R—COOH over chitosan-amine and EDC:NHS:R—COOH may be pre-calculated and satisfied to have reproducible final functionalization degree of arginine. Boc-R-chitosan may be purified prior to the De-Boc reaction. De-Boc may proceed in HCl medium with a controlled HCl concentration and reaction time. Any depolymerization of chitosan during de-Boc may be monitored by measuring the viscosity of the reaction solution, which was proven to be negligible, and the efficiency of de-Boc may be ascertained by proton NMR on de-Boc-R-chitosan and Boc-R-chitosan. The functionalization degree may be determined from C, N elemental analysis of the purified de-Boc-R-chitosan.

Gluconic acid may be coupled to chitosan or arginine-coupled chitosan (R-chitosan) at a reaction pH of 6.0±0.3. At this pH, the carboxylic acid group of gluconic acid may be attacked by uncoupled amines on the chitosan backbone according to a nucleophilic substitution reaction mechanism. An ordinarily skilled artisan will recognize that, when coupling gluconic acid to R-chitosan, it is also possible that a small amount of gluconic acid may form a covalent bond with the amine group of arginine through the same mechanism, although it is likely that the nucleophilic substitution reaction will occur predominantly with the amine group of the chitosan backbone. As such, in certain embodiments, $R^1$ of Formula I may also be independently selected from hydrogen, acetyl, Formula (II), Formula (III), and Formula (IV).

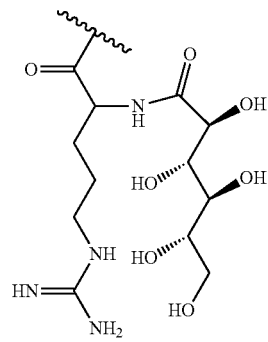

(IV)

Boc-R-chitosan, de-Boc-R-chitosan, gluco-chitosan, and/or dually derivatized chitosan may be purified via precipitation, or column treatment, or regular dialysis, or inverse-flow dialysis against Milli-Q water using cellulose dialysis tubing of appropriate molecular weight cut off (MWCO), or through a tangential-flow-filtration (TFF) and diafiltration cartridges.

Accordingly, "dually derivatized-chitosan" or "DD-chitosan" also refers to chitosan that has been dually functionalized ("dually functionalized-chitosan" or "DF-chitosan), e.g., coupled with both arginine and gluconic acid, both of which are covalently attached to chitosan. The arginine may be covalently attached to chitosan either as single amino acid or as a polypeptide.

As used herein, unless otherwise indicated, the term "peptide" and "polypeptide" are used interchangeably.

The term "polypeptide" is used in its broadest sense to refer to conventional polypeptides (i.e., short polypeptides containing L or D-amino acids), as well as peptide equivalents, peptide analogs and peptidomimetics that retain the desired functional activity. Peptide equivalents can differ from conventional peptides by the replacement of one or more amino acids with related organic acids, amino acids or the like, or the substitution or modification of side chains or functional groups.

Peptidomimetics may have one or more peptide linkages replaced by an alternative linkage, as is known in the art. Portions or all of the peptide backbone can also be replaced by conformationally constrained cyclic alkyl or aryl substituents to restrict mobility of the functional amino acid sidechains, as is known in the art.

The polypeptides of this invention may be produced by recognized methods, such as recombinant and synthetic methods that are well known in the art. Techniques for the synthesis of peptides are well known and include those described in Merrifield, J. Amer. Chem. Soc. 85:2149-2456 (1963), Atherton, et al., Solid Phase Peptide Synthesis: A Practical Approach, IRL Press (1989), and Merrifield, Science 232:341-347 (1986).

As used herein, "linear polypeptide" refers to a polypeptide that lacks branching groups covalently attached to its constituent amino acid side chains. As used herein, "branched polypeptide" refers to a polypeptide that comprises branching groups covalently attached to its constituent amino acid side chains.

As used herein, the term "amino acid" includes naturally occurring amino acids as well as non-naturally occurring amino acids such as amino acid analogs. The term "amino acid" refers to naturally occurring (D) or (L) amino acids, chemically modified amino acids, naturally occurring amino acids such as norleucine and chemically synthesized compounds that have properties known in the art to be characteristic of an amino acid.

Amino acid residues in peptides are abbreviated as is standard in the art.

In some embodiments, where appropriate, DD-chitosan includes DD-chitosan derivatives, e.g., DD chitosan that incorporate an additional functionalization, e.g., DD-chitosan with an attached ligand. "Derivatives" will be understood to include the broad category of chitosan-based polymers comprising covalently modified N-acetyl-D-glucosamine and/or D-glucosamine units, as well as chitosan-based polymers incorporating other units, or attached to other moieties. Derivatives are frequently based on a modification of the hydroxyl group or the amine group of glucosamine, such as done with arginine-functionalized chitosan. Examples of chitosan derivatives include, but are not limited to, trimethylated chitosan, PEGylated chitosan, thiolated chitosan, galactosylated chitosan, alkylated chitosan, PEI-incorporated chitosan, uronic acid modified chitosan, glycol chitosan, and the like. For further teaching on chitosan derivatives, see, for example, pp. 63-74 of "Non-viral Gene Therapy", K. Taira, K. Kataoka, T. Niidome (editors), Springer-Verlag Tokyo, 2005, ISBN 4-431-25122-7; Zhu et al., Chinese Science Bulletin, December 2007, vol. 52 (23), pp. 3207-3215; and Varma et al., Carbohydrate Polymers 55 (2004) 77-93.

Dispersed systems consist of particulate matter, known as the dispersed phase, distributed throughout a continuous medium. A "dispersion" of DD-chitosan nucleic acid polyplexes is a composition comprising hydrated DD-chitosan nucleic acid polyplexes, wherein polyplexes are distributed throughout the medium.

As used herein, a "pre-concentrated" dispersion is one that has not undergone the concentrating process to form a concentrated dispersion.

As used herein, "substantially free" of polyplex precipitate means that the composition is essentially free from particles that can be observed on visual inspection.

As used herein, physiological pH refers to a pH between 6 to 8.

By "DD-chitosan nucleic acid polyplex" or its grammatical equivalents is meant a complex comprising a plurality of DD-chitosan molecules and a plurality of nucleic acid molecules. In a preferred embodiment, the dually derivatized-chitosan is complexed with said nucleic acid.

The DD-chitosan nucleic acid polyplexes comprise a nucleic acid component and a DD-chitosan component. Chitosan, and DD-chitosan nucleic acid polyplexes may be prepared by any method known in the art. For example, functionalized chitosan and nucleotide feedstock concentrations may be adjusted to accommodate various amine-to-phosphate ratios (N/P), mixing ratios and target nucleotide concentrations. In some embodiments, particularly small batches, e.g., batches under 2 mL, the functionalized chitosan and nucleotide feedstocks may be mixed by slowly dripping the nucleotide feedstock into the functionalized chitosan feedstock while vortexing the container. In other embodiments, the functionalized chitosan and nucleotide feedstocks may be mixed by in-line mixing the two fluid streams. In other embodiments, the resulting polyplex dispersion may be concentrated by TFF. A preferred method for polyplex formation is disclosed in WO 2009/039657, which is expressly incorporated herein in its entirety by reference.

A nucleic acid of the present invention will generally contain phosphodiester bonds, although in some cases nucleic acid analogs are included that may have alternate backbones or other modifications or moieties incorporated for any of a variety of purposes, e.g., stability and protection. Other analog nucleic acids contemplated include those with non-ribose backbones. In addition, mixtures of naturally occurring nucleic acids, analogs, and both can be made. The nucleic acids may be single stranded or double stranded or contain portions of both double stranded or single stranded sequence. Nucleic acids include but are not limited to DNA, RNA and hybrids where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. Nucleic acids include DNA in any form, RNA in any form, including triplex, duplex or single-stranded, anti-sense, siRNA, ribozymes, deoxyribozymes, polynucleotides, oligonucleotides, chimeras, microRNA, and derivatives thereof. Nucleic acids include artificial nucleic acids, including but not limited to, peptide nucleic acid (PNA), phosphorodiamidate morpholino oligo (PMO), locked nucleic acid (LNA), glycol nucleic acid (GNA) and threose nucleic acid (TNA).

In one embodiment, the nucleic acid component comprises a therapeutic nucleic acid. The subject DD-chitosan nucleic acid polyplexes are amenable to the use of any therapeutic nucleic acid known in the art. Therapeutic nucleic acids include therapeutic RNAs, which are RNA molecules capable of exerting a therapeutic effect in a mammalian cell. Therapeutic RNAs include, but are not limited to, antisense RNAs, siRNAs, short hairpin RNAs, micro RNAs, and enzymatic RNAs. Therapeutic nucleic acids include, but are not limited to, nucleic acids intended to form triplex molecules, protein binding nucleic acids, ribozymes, deoxyribozymes, and small nucleotide molecules.

Many types of therapeutic RNAs are known in the art. For example, see Grimm et al., Therapeutic application of RNAi: is mRNA targeting finally ready for prime time? J. Clin. Invest., 117:3633-3641, 2007; Aagaard et al., RNAi therapeutics: Principles, prospects and challenges, Adv. Drug Deliv. Rev., 59:75-86, 2007; Dorsett et al., siRNAs: Applications in functional genomics and potential as therapeutics, Nat. Rev. Drug Discov., 3:318-329, 2004. These include double-stranded short interfering RNA (siRNA).

Therapeutic nucleic acids also include nucleic acids encoding therapeutic proteins, including cytotoxic proteins and prodrugs.

In a preferred embodiment, the nucleic acid component comprises a therapeutic nucleic acid construct. The therapeutic nucleic acid construct is a nucleic acid construct capable of exerting a therapeutic effect. Therapeutic nucleic acid constructs may comprise nucleic acids encoding therapeutic proteins, as well as nucleic acids that produce transcripts that are therapeutic RNAs. A therapeutic nucleic acid may be used to effect genetic therapy by serving as a replacement or enhancement for a defective gene or to compensate for lack of a particular gene product, by encoding a therapeutic product. A therapeutic nucleic acid may also inhibit expression of an endogenous gene. A therapeutic nucleic acid may encode all or a portion of a translation product, and may function by recombining with DNA already present in a cell, thereby replacing a defective portion of a gene. It may also encode a portion of a protein and exert its effect by virtue of co-suppression of a gene product. In a preferred embodiment, the therapeutic nucleic acid is selected from those disclosed in U.S. Ser. No. 11/694,852, which is expressly incorporated herein by reference.

In a preferred embodiment, the therapeutic nucleic acid encodes a therapeutic protein that is selected from the group consisting of hormones, enzymes, cytokines, chemokines, antibodies, mitogenic factors, growth factors, differentiation factors, factors influencing angiogenesis, factors influencing blood clot formation, factors influencing blood glucose levels, factors influencing glucose metabolism, factors influencing lipid metabolism, factors influencing blood cholesterol levels, factors influencing blood LDL or HDL levels, factors influencing cell apoptosis, factors influencing food intake, factors influencing energy expenditure, factors influencing appetite, factors influencing nutrient absorption, factors influencing inflammation, and factors influencing bone formation. Particularly preferred are therapeutic nucleic acids encoding insulin, leptin, glucagon antagonist, GLP-1, GLP-2, Ghrelin, cholecystokinin, growth hormone, clotting factors, PYY, erythropoietin, inhibitors of inflammation, IL-10, IL-17 antagonists, TNFα antagonists, growth hormone releasing hormone, or parathyroid hormone.

Expression Control Regions

In a preferred embodiment, a polyplex of the invention comprises a therapeutic nucleic acid, which is a therapeutic construct, comprising an expression control region operably linked to a coding region. The therapeutic construct produces therapeutic nucleic acid, which may be therapeutic on its own, or may encode a therapeutic protein.

In some embodiments, the expression control region of a therapeutic construct possesses constitutive activity. In a number of preferred embodiments, the expression control region of a therapeutic construct does not have constitutive activity. This provides for the dynamic expression of a therapeutic nucleic acid. By "dynamic" expression is meant expression that changes over time. Dynamic expression may include several such periods of low or absent expression separated by periods of detectable expression. In a number of preferred embodiments, the therapeutic nucleic acid is operably linked to a regulatable promoter. This provides for the regulatable expression of therapeutic nucleic acids.

Expression control regions comprise regulatory polynucleotides (sometimes referred to herein as elements), such as promoters and enhancers, which influence expression of an operably linked therapeutic nucleic acid.

Expression control elements included herein can be from bacteria, yeast, plant, or animal (mammalian or non-mammalian). Expression control regions include full-length promoter sequences, such as native promoter and enhancer elements, as well as subsequences or polynucleotide variants that retain all or part of full-length or non-variant function (e.g., retain some amount of nutrient regulation or cell/tissue-specific expression). As used herein, the term "functional" and grammatical variants thereof, when used in reference to a nucleic acid sequence, subsequence or fragment, means that the sequence has one or more functions of native nucleic acid sequence (e.g., non-variant or unmodified sequence). As used herein, the term "variant" means a sequence substitution, deletion, or addition, or other modification (e.g., chemical derivatives such as modified forms resistant to nucleases).

As used herein, the term "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Some expression control regions confer regulatable expression to an operatably linked therapeutic nucleic acid. A signal (sometimes referred to as a stimulus) can increase or decrease expression of a therapeutic nucleic acid operatably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Numerous regulatable promoters are known in the art. Preferred inducible expression control regions include those comprising an inducible promoter that is stimulated with a small molecule chemical compound. In one embodiment, an expression control region is responsive to a chemical that is orally deliverable but not normally found in food. Particular examples can be found, for example, in U.S. Pat. Nos. 5,989,910; 5,935,934; 6,015,709; and 6,004,941.

In one embodiment, the therapeutic construct further comprises an integration sequence. In one embodiment, the therapeutic construct comprises a single integration sequence. In another embodiment, the therapeutic construct comprises a first and a second integration sequence for integrating the therapeutic nucleic acid or a portion thereof into the genome of a target cell. In a preferred embodiment, the integration sequence(s) is functional in combination with a means for integration that is selected from the group consisting of mariner, sleeping beauty, FLP, Cre, ΦC31, R, lambda, and means for integration from integrating viruses such as AAV, retroviruses, and lentiviruses.

In one embodiment, the subject composition further comprises a non-therapeutic construct in addition to a therapeutic construct, wherein the non-therapeutic construct comprises a nucleic acid sequence encoding a means for integration operably linked to a second expression control region. This second expression control region and the expression control region operably linked to the therapeutic nucleic acid may be the same or different. The encoded means for integration is preferably selected from the group consisting of mariner, sleeping beauty, FLP, Cre, ΦC31, R, lambda, and means for integration from integrating viruses such as AAV, retroviruses, and lentiviruses.

For further teaching, see WO2008020318, which is expressly incorporated herein in its entirety by reference. In one embodiment, the nucleic acid of the DD-chitosan nucleic acid polyplex is an artificial nucleic acid.

Preferred artificial nucleic acids include, but are not limited to, peptide nucleic acid (PNA), phosphorodiamidate morpholino oligo (PMO), locked nucleic acid (LNA), glycol nucleic acid (GNA) and threose nucleic acid (TNA).

In one embodiment, the nucleic acid of the DD-chitosan nucleic acid polyplex is a therapeutic nucleic acid. In one embodiment, the therapeutic nucleic acid is a therapeutic RNA. Preferred therapeutic RNAs include, but are not limited to, antisense RNA, siRNA, short hairpin RNA, micro RNA, and enzymatic RNA.

In one embodiment, the therapeutic nucleic acid is DNA.

In one embodiment, the therapeutic nucleic acid comprises a nucleic acid sequence encoding a therapeutic protein.

Polyplexes

In a preferred embodiment, the polyplexes of the compositions comprise chitosan molecules having an average molecular weight of less than 110 kDa, more preferably less than 65 kDa, more preferably less than 50 kDa, more preferably less than 40 kDa, and most preferably less than 30 kDa before functionalization. In some embodiments, polyplexes of the compositions comprise chitosan having an average molecular weight of less than 15 kDa, less than 10 kDa, less than 7 kDa, or less than 5 kDa before functionalization.

In a preferred embodiment, the polyplexes comprise chitosan molecules having on average less than 680 glucosamine monomer units, more preferably less than 400 glucosamine monomer units, more preferably less than 310 glucosamine monomer units, more preferably less than 250 glucosamine monomer units, and most preferably less than 190 glucosamine monomer units. In some embodiments, the polyplexes comprise chitosan molecules having on average less than 95 glucosamine monomer units, less than 65 glucosamine monomer units, less than 45 glucosamine monomer units, or less than 35 glucosamine monomer units.

In a preferred embodiment, the subject polyplexes have amine to phosphate (N/P) ratio of 2 to 100, e.g., 2 to 50, e.g., 2 to 40, e.g., 2 to 30, e.g., 2 to 20, e.g., 2 to 5. Preferably, the N/P ratio is inversely proportional to the molecular weight of the chitosan, i.e., a smaller molecular weight DD-chitosan requires a higher N/P ratio, and vice-versa.

In a preferred embodiment, the subject polyplexes have an average hydrodynamic diameter of less than 1000 nm, more preferably less than 500 nm and most preferably less than 200 nm.

In one embodiment, the DD-chitosan nucleic acid polyplexes have an average zeta potential of at least 0 mV at an acidic pH, e.g., a pH below 7, most preferably a pH between about 4 to 6.

In one embodiment, the DD-chitosan nucleic acid polyplexes have an average zeta potential between +1 to +60 mV, more preferably +1 to +40 mV, more preferably +1 to +30 mV at an acidic pH.

In a preferred embodiment, the polypeptide has a low net positive, neutral, or net negative charge at physiological pH and a pKa below 6. Such DD-chitosan nucleic acid polyplexes exhibit reduced cellular toxicity and enhanced intracellular release of nucleic acid.

The DD-chitosan nucleic acid polyplexes of the composition are preferably homogeneous in respect of polyplex size. Accordingly, in a preferred embodiment, the composition has a low average polydispersity index ("PDI"). In an especially preferred embodiment, the DD-chitosan nucleic acid polyplex dispersion has a PDI of less than 0.5, more preferably less than 0.4, more preferably less than 0.3, and most preferably less than 0.25.

The polyplexes of the subject compositions are preferably substantially size stable in the composition. In a preferred embodiment, a composition of the invention comprises polyplexes that increase in average diameter by less than 100%, more preferably less than 50%, and most preferably less than 25%, at room temperature for 6 hours, more preferably 12 hours, more preferably 24 hours, and most preferably 48 hours.

The polyplexes of the subject compositions are preferably substantially size stable under cooled conditions. In a preferred embodiment, a composition of the invention comprises polyplexes that increase in average diameter by less than 100%, more preferably less than 50%, and most preferably less than 25%, at 2-8 degrees Celsius for 6 hours, more preferably 12 hours, more preferably 24 hours, and most preferably 48 hours.

The polyplexes of the subject compositions are preferably substantially size stable under freeze-thaw conditions. In a preferred embodiment, a composition of the invention comprises polyplexes that increase in average diameter by less than 100%, more preferably less than 50%, and most preferably less than 25% at room temperature for 6 hours, more preferably 12 hours, more preferably 24 hours, and most preferably 48 hours following thaw from frozen at −20 to −80 degrees Celsius.

In a preferred embodiment, the composition has a nucleic acid concentration greater than 0.5 mg/ml, and is substantially free of precipitated polyplex. More preferably, the composition has a nucleic acid concentration of at least 0.6 mg/ml, more preferably at least 0.75 mg/ml, more preferably at least 1.0 mg/ml, more preferably at least 1.2 mg/ml, and most preferably at least 1.5 mg/ml, and is substantially free of precipitated polyplex. The compositions are hydrated. In a preferred embodiment, the composition is substantially free of uncomplexed nucleic acid.

In a preferred embodiment, the DD-chitosan nucleic acid polyplex composition is isotonic. Achieving isotonicity, while maintaining polyplex stability, is highly desirable in formulating pharmaceutical compositions, and these preferred compositions are well suited to pharmaceutical formulation and therapeutic applications.

Generally, compositions comprising the DD-chitosan nucleic acid polyplexes are used to contact a target cell. Such contact generally results in delivery of the nucleic acid for expression by the targeted cell. Compositions suitable for the DD-chitosan nucleic acid polyplexes described herein are well-known in the art, and are generally described below.

Powdered Formulations

The DD-chitosan nucleic acid polyplex compositions of the invention include powders. In a preferred embodiment, the invention provides a dry powder DD-chitosan nucleic acid polyplex composition. In a preferred embodiment, the dry powder DD-chitosan nucleic acid polyplex composition is produced through the dehydration of a chitosan-nucleic acid polyplex dispersion of the invention.

Pharmaceutical Formulations

The present invention also provides "pharmaceutically acceptable" or "physiologically acceptable" formulations comprising DD-chitosan nucleic acid polyplex compositions of the invention. Such formulations can be administered in vivo to a subject in order to practice treatment methods.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

Excipients can include a salt, an isotonic agent, a serum protein, a buffer or other pH-controlling agent, an antioxidant, a thickener, an uncharged polymer, a preservative or a cryoprotectant. Excipients used in compositions of the invention may further include an isotonic agent and a buffer or other pH-controlling agent. These excipients may be added for the attainment of preferred ranges of pH (about 6.0-8.0) and osmolarity (about 50-300 mmol/L). Examples of suitable buffers are acetate, borate, carbonate, citrate, phosphate and sulfonated organic molecule buffer. Such buffers may be present in a composition in concentrations from 0.01 to 1.0% (w/v). An isotonic agent may be selected from any of those known in the art, e.g. mannitol, dextrose, glucose and sodium chloride, or other electrolytes. Preferably, the isotonic agent is glucose or sodium chloride. The isotonic agents may be used in amounts that impart to the composition the same or a similar osmotic pressure as that of the biological environment into which it is introduced. The concentration of isotonic agent in the composition will depend upon the nature of the particular isotonic agent used and may range from about 0.1 to 10%. When glucose is used, it is preferably used in a concentration of from 1 to 5% w/v, more particularly 5% w/v. When the isotonic agent is sodium chloride, it is preferably employed in amounts of up to 1% w/v, in particular 0.9% w/v. The compositions of the invention may further contain a preservative. Examples preservatives are polyhexamethylene-biguanidine, benzalkonium chloride, stabilized oxychloro complexes (such as those known as PuriteR), phenylmercuric acetate, chlorobutanol, sorbic acid, chlorhexidine, benzyl alcohol, parabens, and thimerosal. Typically, such preservatives are present at concentrations from about 0.001 to 1.0%. Furthermore, the compositions of the invention may also contain a cryopreservative agent. Preferred cryopreservatives are glucose, sucrose, mannitol, lactose, trehalose, sorbitol, colloidal silicon dioxide, dextran of molecular weight preferable below 100,000 g/mol, glycerol, and polyethylene glycols of molecular weights below 100,000 g/mol or mixtures thereof. Most preferred are glucose, trehalose and polyethylene glycol. Typically, such cryopreservatives are present at concentrations from about 0.01 to 10%.

A pharmaceutical formulation can be formulated to be compatible with its intended route of administration. For example, for oral administration, a composition can be incorporated with excipients and used in the form of tablets, troches, capsules, e.g., gelatin capsules, or coatings, e.g., enteric coatings (Eudragit® or Sureteric®). Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Suppositories and other rectally administrable formulations (e.g., those administrable by enema) are also contemplated. Further regarding rectal delivery, see, for example, Song et al., Mucosal drug delivery: membranes, methodologies, and applications, Crit. Rev. Ther. Drug. Carrier Syst., 21:195-256, 2004; Wearley, Recent progress in protein and peptide delivery by noninvasive routes, Crit. Rev. Ther. Drug. Carrier Syst., 8:331-394, 1991.

Additional pharmaceutical formulations appropriate for administration are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

Administration

In one embodiment, the use of DD-chitosan in DD-chitosan nucleic acid polyplexes provides for prolonged stability of polyplexes at physiological pH. This provides for effective systemic administration, as well as other modes of administration.

Any of a number of administration routes are possible and the choice of a particular route will in part depend on the target tissue. Syringes, endoscopes, cannulas, intubation tubes, catheters and other articles may be used for administration.

The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Thus, in the case of a condition or disorder treatable by expressing a therapeutic nucleic acid in target tissue, the amount of therapeutic RNA or therapeutic protein produced to ameliorate a condition treatable by a method of the invention will depend on the condition and the desired outcome and can be readily ascertained by the skilled artisan. Appropriate amounts will depend upon the condition treated, the therapeutic effect desired, as well as the individual subject (e.g., the bioavailability within the subject, gender, age, etc.). The effective amount can be ascertained by measuring relevant physiological effects.

Veterinary applications are also contemplated by the present invention. Accordingly, in one embodiment, the invention provides methods of treating non-human mammals, which involve administering a chitosan-based nanoparticle of the invention to a non-human mammal in need of treatment.

Parenteral Administration

The compounds of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents, but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound.

Oral Administration

The subject compositions may be administered orally. Oral administration may involve swallowing, so that the compound enters the gastrointestinal tract. Compositions of the invention may also be administered directly to the gastrointestinal tract.

Formulations suitable for oral administration include solid formulations such as tablets, capsules, coated capsules containing particulates or coated particulates, liquids, or powders, lozenges (including liquid-filled), chews, multi- and nano-particulates, gels, films, ovules, and sprays.

Liquid formulations include suspensions, solutions, syrups and elixirs. Liquid formulations may be prepared by the reconstitution of a solid.

Tablet dosage forms generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a film-forming polymer, a binder, a solvent, a humectant, a plasticiser, a stabiliser or emulsifier, a viscosity-modifying agent and a solvent. Some components of the formulation may perform more than one function.

Also included in the invention are multiparticulate beads comprising a composition of the invention.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Other suitable release technologies such as high energy dispersions and osmotic and coated particles are known.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions.

Other means of topical administration include delivery by electroporation, iontophoresis, phonophoresis, sonophoresis and microneedle or needle-free (e.g. Powderject™ Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle) from a dry powder inhaler or as an aerosol spray from a pressurized container, pump, spray, atomiser, or nebuliser, with or without the use of a suitable propellant.

Capsules, blisters and cartridges for use in an inhaler or insufflator may be formulated to contain a powder mix of the compound of the invention, a suitable powder base such as lactose or starch and a performance modifier such as I-leucine, mannitol, or magnesium stearate.

Formulations for inhaled/intranasal administration may be formulated to be immediate and/or modified release. Modified release formulations include delayed-, sustained-, pulsed-, controlled-, targeted and programmed release.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops. Other formulations suitable for ocular and aural administration include ointments, biodegradable (e.g. absorbable gel sponges, collagen) and non-biodegradable (e.g. silicone) implants, wafers, lenses and particulate systems. Formulations may also be delivered by iontophoresis.

Formulations for ocular/aural administration may be formulated to be immediate and/or modified release. Modified release formulations include delayed-, sustained-, pulsed-, controlled-, targeted, or programmed release.

Methods of Use

In one embodiment, DD-chitosan nucleic acid polyplex compositions of the invention may be used for therapeutic treatment. Such compositions are sometimes referred to herein as therapeutic compositions.

Therapeutic proteins of the invention, as discussed below, are produced by polyplexes of the invention comprising therapeutic nucleic acids. Use of the subject proteins as described below refers to use of the subject polyplexes to effect such protein use.

Therapeutic proteins contemplated for use in the invention have a wide variety of activities and find use in the treatment of a wide variety of disorders. The following description of therapeutic protein activities, and indications treatable with therapeutic proteins of the invention, is exemplary and not intended to be exhaustive. The term "subject" refers to an animal, with mammals being preferred, and humans being especially preferred.

A partial list of therapeutic proteins and target diseases is shown in Table 1.

TABLE 1

| LEAD COMPOUNDS | TARGET DISEASE | FUNCTION | THERAPEUTIC EFFECT |
|---|---|---|---|
| Insulin | Diabetes | Insulin replacement | Improve glucose tolerance. Delay/prevent diabetes. |
| Glucagon antagonists | Diabetes | Reduce endogenous glucose production | Improve glucose tolerance |
| GLP-1 | Diabetes Obesity | Stimulate growth of β-cells, improve insulin sensitivity, suppress appetite | Improve glucose tolerance. Induce weight loss |
| Leptin | Obesity Diabetes | Appetite suppression and improvement of insulin sensitivity | Induce weight loss. Improve glucose tolerance |
| CCK | Obesity | Appetite suppression | Induce weight loss |
| Growth Hormone (GH) | GH deficiencies, wasting and anti-aging | GH replacement | Improve growth |
| Clotting factors | Hemophilia | Clotting factors replacement | Improve clotting time |
| Therapeutic antibodies and antibody fragments/portions | Infections Cancer | Pathogen neutralization or immune modulations | Prevent infections or transplant rejections |
| Inflammation inhibitors, e.g., IL-10, TNFα antagonists, IL-17 antagonists | Gastrointestinal organ inflammation; e.g., inflammatory bowel disease (IBD) | Immune modulation | Prevent inflammation in Gastrointestinal organ |

In another embodiment, therapeutic compositions of the invention comprise therapeutic nucleic acids that do not encode therapeutic proteins, e.g., therapeutic RNAs, For example, by selecting therapeutic RNAs that target genes involved in mechanisms of disease and/or undesirable cellular or physiological conditions, the subject compositions may be used in the treatment of a wide array of diseases and conditions. The subject compositions are of such character that the therapeutic RNAs used are not limited in respect of the scope of target selection. Accordingly, the subject compositions find use in any disease or condition involving a suitable target.

Preferred tissues, diseases, and conditions include the following, which are exemplary and in no way limiting:

| Target Organ | Target Disease |
|---|---|
| Gastrointestinal (GI) organs | Diabetes Obesity Inflammatory bowel disease Irritible bowel syndrome GI infection Peptic ulcers Gastroesophageal reflux Gastriparesis |

| Target Organ | Target Disease |
|---|---|
| | Hemorrhoids |
| | Malabsorption of nutrients |
| | GI cancers (colorectal, pancreatic, stomach, esophageal, bile duct, gall bladder cancers) |
| | Pancreatitis |
| | Hemochromatosis |
| | Celiac disease |
| | Food allergies |
| | Immune tolerance induction |
| Eye | Macular degeneration |
| | Age-related macular degeneration |
| | Uveitis |
| | Retinitis pigmentosa |
| | Iritis |
| | Scleritis |
| | Glaucoma |
| | Keratititis |
| | Retinopathy |
| | Eye infection (e.g. keratomycosis) |
| Uterus, vagina, ovary and cervix | Cancers |
| | Infections |
| | Endometriosis |
| | Cervicitis |
| | Urologic pain |
| | Polyps |
| | Fibroids |
| | Endometrial hyperplasia |
| Bladder and urinary tract | Urinary incontinence |
| | Bladder and urinary tract infection |
| | Overactive bladder |
| | Erectile dysfunction |
| | Diabetic neuropathy |
| Kidney | Diabetic nephropathy |
| | Membranous nephropathy |
| | Hypertension |
| | Renal cancer |
| | Hypertension |
| | Polycystic kidney disease |
| | Glomerulonephritis |
| Liver | Dyslipidemia/hypercholesterolemia |
| | Diabetes |
| | Metabolic syndrome |
| | Hepatoma |
| | Hepatitis A/B/C |
| | Hemochromatosis |
| | Cirrhosis |
| | Steatohepatitis |
| | Glycogen storage diseases |
| Skin | Psoriasis |
| | Acne |
| | Rosacea |
| | Granulomatous dermatitis |
| | Anti-wrinkle |
| | Depigmentation |
| Lung/ Respiratory organs | Lung cancer |
| | Chronic obstructive pulmonary disease |
| | Respiratory tract infection |
| | Cystic fibrosis |
| | Pulmonary vascular diseases |
| | Myasthenia gravis |
| | Fibrosis |
| | Asthma |
| Brain | Huntington's disease |
| | Alzheimer disease |
| | Parkinson's disease |
| | Brain cancer |
| | Obesity |
| | Neurological disorders |
| Blood cells | Cancers |
| | Infectious disease |
| | Autoimmune disease |
| Muscle | Metabolic syndrome |
| | Atherosclerosis |
| | Diabetes |
| | Sarcoma |
| | Inflammation (e.g. polymyositis) |
| | Glycogen storage diseases |
| | Myopathy |
| Heart | Myocardial infarction |
| | Atherosclerosis |
| | Angina |
| | Cardiomyopathy |
| | Ischemia |
| | Hypertensive heart diseases |
| | Thrombosis |
| | Aneurysm |
| Adipose | Diabetes |
| | Obesity |
| | Metabolic syndrome |
| | Atherosclerosis |
| | Dyslipidemia |

Hyperglycemia and Body Mass

Therapeutic proteins include insulin and insulin analogs. Diabetes mellitus is a debilitating metabolic disease caused by absent (type 1) or insufficient (type 2) insulin production from pancreatic β-cells (Unger, R. H. et al., Williams Textbook of Endocrinology Saunders, Philadelphia (1998)). Beta-cells are specialized endocrine cells that manufacture and store insulin for release following a meal (Rhodes, et. al. J. Cell Biol. 105:145 (1987)) and insulin is a hormone that facilitates the transfer of glucose from the blood into tissues where it is needed. Patients with diabetes must frequently monitor blood glucose levels and many require multiple daily insulin injections to survive. However, such patients rarely attain ideal glucose levels by insulin injection (Turner, R. C. et al. JAMA 281:2005 (1999)). Furthermore, prolonged elevation of insulin levels can result in detrimental side effects such as hypoglycemic shock and desensitization of the body's response to insulin. Consequently, diabetic patients still develop long-term complications, such as cardiovascular diseases, kidney disease, blindness, nerve damage and wound healing disorders (UK Prospective Diabetes Study (UKPDS) Group, Lancet 352, 837 (1998)).

Disorders treatable by a method of the invention include a hyperglycemic condition, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular examples include degeneration of pancreas (β-cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension and obesity.

The subject compositions are useful for decreasing glucose, improving glucose tolerance, treating a hyperglycemic condition (e.g., diabetes) or for treating a physiological disorders associated with or resulting from a hyperglycemic condition. Such disorders include, for example, diabetic neuropathy (autonomic), nephropathy (kidney damage), skin infections and other cutaneous disorders, slow or delayed healing of injuries or wounds (e.g., that lead to diabetic carbuncles), eye damage (retinopathy, cataracts) which can lead to blindness, diabetic foot and accelerated periodontitis. Such disorders also include increased risk of developing coronary heart disease, stroke, peripheral vascular disease, dyslipidemia, hypertension and obesity.

As used herein, the term "hyperglycemic" or "hyperglycemia," when used in reference to a condition of a subject, means a transient or chronic abnormally high level of glucose present in the blood of a subject. The condition can be caused by a delay in glucose metabolization or absorption such that the subject exhibits glucose intolerance or a state of elevated glucose not typically found in normal subjects (e.g., in glucose-intolerant subdiabetic subjects at risk of developing diabetes, or in diabetic subjects). Fasting plasma glucose (FPG) levels for normoglycemia are less than about 110 mg/dl, for impaired glucose metabolism, between about 110 and 126 mg/dl, and for diabetics greater than about 126 mg/dl.

Disorders treatable by producing a protein in a gut mucosal tissue also include obesity or an undesirable body mass. Leptin, cholecystokinin, PYY and GLP-1 decrease hunger, increase energy expenditure, induce weight loss or provide normal glucose homeostasis. Thus, in various embodiments, a method of the invention for treating obesity or an undesirable body mass, or hyperglycemia, involves the use of a therapeutic nucleic acid encoding leptin, cholecystokinin, PYY or GLP-1. In another embodiment, a therapeutic RNA targeting ghrelin is used. Ghrelin increases appetite and hunger. Thus, in various embodiments, a method of the invention for treating obesity or an undesirable body mass, or hyperglycemia, involves the use of a therapeutic RNA targeting ghrelin to decrease the expression thereof. Disorders treatable also include those typically associated with obesity, for example, abnormally elevated serum/plasma LDL, VLDL, triglycerides, cholesterol, plaque formation leading to narrowing or blockage of blood vessels, increased risk of hypertension/stroke, coronary heart disease, etc.

As used herein, the term "obese" or "obesity" refers to a subject having at least a 30% increase in body mass in comparison to an age and gender matched normal subject. "Undesirable body mass" refers to subjects having 1%-29% greater body mass than a matched normal subject as well as subjects that are normal with respect to body mass but who wish to decrease or prevent an increase in their body mass.

In one embodiment, a therapeutic protein of the invention is a glucagon antagonist. Glucagon is a peptide hormone produced by β-cells in pancreatic islets and is a major regulator of glucose metabolism (Unger R. H. & Orci L. N. Eng. J. Med. 304:1518 (1981); Unger R. H. Diabetes 25:136 (1976)). As with insulin, blood glucose concentration mediates glucagon secretion. However, in contrast to insulin glucagon is secreted in response to a decrease in blood glucose. Therefore, circulating concentrations of glucagon are highest during periods of fast and lowest during a meal. Glucagon levels increase to curtail insulin from promoting glucose storage and stimulate liver to release glucose into the blood. A specific example of a glucagon antagonist is [des-His1, des-Phe6, Glu9]glucagon-NH2. In streptozotocin diabetic rats, blood glucose levels were lowered by 37% within 15 min of an intravenous bolus (0.75 μg/g body weight) of this glucagon antagonist (Van Tine B. A. et. al. Endocrinology 137:3316 (1996)). In another embodiment, the invention provides a method for treating diabetes or hyperglycemia, comprising the use of a therapeutic RNA to decrease the levels of glucagon production from the pancreas.

In another embodiment, a therapeutic protein of the invention useful for treating a hyperglycemic condition or undesirable body mass (e.g., obesity) is a glucagon-like peptide-1 (GLP-1). GLP-1 is a hormone released from L-cells in the intestine during a meal which stimulates pancreatic β-cells to increase insulin secretion. GLP-1 has additional activities that make it an attractive therapeutic agent for treating obesity and diabetes. For example, GLP-1 reduces gastric emptying, suppresses appetite, reduces glucagon concentration, increases β-cell mass, stimulates insulin biosynthesis and secretion in a glucose-dependent fashion, and likely increases tissue sensitivity to insulin (Kieffer T. J., Habener J. F. Endocrin. Rev. 20:876 (2000)). Therefore, regulated release of GLP-1 in the gut to coincide with a meal can provide therapeutic benefit for a hyperglycemic condition or an undesirable body mass. GLP-1 analogs that are resistant to dipeptidyl peptidate IV (DPP IV) provide longer duration of action and improved therapeutic value. Thus, GLP-1 analogs are preferred therapeutic polypeptides. In another embodiment, the invention provides a method for treating diabetes or hyperglycemia, comprising the use of a therapeutic RNA to decrease the levels of DPP IV.

In another embodiment, a therapeutic protein of the invention useful for treating a hyperglycemic condition is an antagonist to the hormone resistin. Resistin is an adipocyte-derived factor for which expression is elevated in diet-induced and genetic forms of obesity. Neutralization of circulating resistin improves blood glucose and insulin action in obese mice. Conversely, administration of resistin in normal mice impairs glucose tolerance and insulin action (Steppan C M et. al. Nature 409:307 (2001)). Production of a protein that antagonizes the biological effects of resistin in gut can therefore provide an effective therapy for obesity-linked insulin resistance and hyperglycemic conditions. In another embodiment, the invention provides a method for treating diabetes or hyperglycemia, comprising the use of a therapeutic RNA to decrease the levels of resistin expression in adipose tissue.

In another embodiment, a therapeutic polypeptide of the invention useful for treating a hyperglycemic condition or undesirable body mass (e.g., obesity) is leptin. Leptin, although produced primarily by fat cells, is also produced in smaller amounts in a meal-dependent fashion in the stomach. Leptin relays information about fat cell metabolism and body weight to the appetite centers in the brain where it signals reduced food intake (promotes satiety) and increases the body's energy expenditure.

In another embodiment, a therapeutic polypeptide of the invention useful for treating a hyperglycemic condition or undesirable body mass (e.g., obesity) is the C-terminal globular head domain of adipocyte complement-related protein (Acrp30). Acrp30 is a protein produced by differentiated adipocytes. Administration of a proteolytic cleavage product of Acrp30 consisting of the globular head domain to mice leads to significant weight loss (Fruebis J. et al. Proc. Natl. Acad. Sci. USA 98:2005 (2001)).

In another embodiment, a therapeutic polypeptide of the invention useful for treating a hyperglycemic condition or undesirable body mass (e.g., obesity) is cholecystokinin (CCK). CCK is a gastrointestinal peptide secreted from the intestine in response to particular nutrients in the gut. CCK release is proportional to the quantity of food consumed and is believed to signal the brain to terminate a meal (Schwartz M. W. et. al. Nature 404:661-71 (2000)). Consequently, elevated CCK can reduce meal size and promote weight loss or weight stabilization (i.e., prevent or inhibit increases in weight gain).

Regarding PYY, see for example le Roux et al., Proc Nutr Soc. 2005 May; 64(2):213-6.

Immunological Disorders

In one embodiment, a therapeutic composition of the invention possesses immunomodulatory activity. For example, a therapeutic polypeptide of the present invention may be useful in treating deficiencies or disorders of the immune system, by activating or inhibiting the proliferation, differentiation, or mobilization (chemotaxis) of immune cells. Immune cells develop through the process of hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g. by chemotherapy or toxins), or infectious.

A therapeutic composition of the present invention may be useful in treating deficiencies or disorders of hematopoietic cells. For example, a therapeutic polypeptide of the present invention could be used to increase differentiation or proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

A therapeutic composition of the present invention may also be useful in treating autoimmune disorders. Many autoimmune disorders result from inappropriate recognition of self as foreign material by immune cells. This inappropriate recognition results in an immune response leading to the destruction of the host tissue. Accordingly, the administration of a therapeutic composition of the present invention that inhibits an immune response, particularly the proliferation, differentiation, or chemotaxis of T-cells, may be an effective therapy in preventing autoimmune disorders.

Examples of autoimmune disorders that can be treated by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin-dependent diabetes mellitus, Crohn's disease, ulcerative colitis, and autoimmune inflammatory eye disease.

Similarly, allergic reactions and conditions, such as asthma (particularly allergic asthma) or other respiratory problems, may also be treated by a therapeutic composition of the present invention. Moreover, these molecules can be used to treat anaphylaxis, hypersensitivity to an antigenic molecule, or blood group incompatibility.

A therapeutic composition of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a therapeutic composition of the present invention that inhibits an immune response, particularly the proliferation, differentiation, or chemotaxis of T-cells, may be an effective therapy in preventing organ rejection or GVHD.

Similarly, a therapeutic composition of the present invention may also be used to modulate inflammation. For example, the therapeutic polypeptide may inhibit the proliferation and differentiation of cells involved in an inflammatory response. These molecules can be used to treat inflammatory conditions, both chronic and acute conditions, including inflammation associated with infection (e.g. septic shock, sepsis, or systemic inflammatory response syndrome (SIRS)), ischemia-reperfusion injury, endotoxin lethality, arthritis, pancreatitis, complement-mediated hyperacute rejection, nephritis, cytokine or chemokine induced lung injury, inflammatory bowel disease (IBD), Crohn's disease, or resulting from over production of cytokines (e.g. TNF or IL-1.) In one embodiment, a therapeutic RNA targeted against TNFα is used in the subject compositions to treat inflammation. In another preferred embodiment, a therapeutic RNA targeted against IL-1 is used in the subject compositions to treat inflammation. siRNA therapeutic RNAs are especially preferred. Inflammatory disorders of interest for treatment in the present invention include, but are not limited to, chronic obstructive pulmonary disorder (COPD), interstitial cystitis, and inflammatory bowel disease.

Clotting Disorders

In some embodiments, a therapeutic composition of the present invention may also be used to modulate hemostatic (the stopping of bleeding) or thrombolytic activity (clot formation). For example, by increasing hemostatic or thrombolytic activity, a therapeutic composition of the present invention could be used to treat blood coagulation disorders (e.g. afibrinogenemia, factor deficiencies), blood platelet disorders (e.g. thrombocytopenia), or wounds resulting from trauma, surgery, or other causes. Alternatively, a therapeutic composition of the present invention that can decrease hemostatic or thrombolytic activity could be used to inhibit or dissolve clotting. These therapeutic compositions could be important in the treatment of heart attacks (infarction), strokes, or scarring. In one embodiment, a therapeutic polypeptide of the invention is a clotting factor, useful for the treatment of hemophilia or other coagulation/clotting disorders (e.g., Factor VIII, IX or X)

Hyperproliferative Disorders

In one embodiment, a therapeutic composition of the invention is capable of modulating cell proliferation. Such a therapeutic polypeptide can be used to treat hyperproliferative disorders, including neoplasms.

Examples of hyperproliferative disorders that can be treated by a therapeutic composition of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated by a therapeutic composition of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Delivery to the circulatory system provides for access of therapeutic protein to a wide variety of tissues. Alternatively, a therapeutic composition of the present invention may stimulate the proliferation of other cells that can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as with a chemotherapeutic agent.

Infectious Disease

In one embodiment, a therapeutic composition of the present invention can be used to treat infectious disease. For example, by increasing the immune response, particularly increasing the proliferation and differentiation of B and/or T cells, infectious diseases may be treated. The immune response may be increased by either enhancing an existing immune response, or by initiating a new immune response. Alternatively, the therapeutic composition of the present invention may also directly inhibit the infectious agent, without necessarily eliciting an immune response.

Viruses are one example of an infectious agent that can cause disease or symptoms that can be treated by a therapeutic composition of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g. Paramyxoviridae, Morbillivirus, Rhabdoviridae), Orthomyxoviridae (e.g. Influenza), Papovaviridae, Parvoviridae, Picornaviridae, Poxyiridae (such as Smallpox or Vaccinia), Reoviridae (e.g. Rotavirus), Retroviridae (HTLV-I, HTLV-II, Lentivirus), and Togaviridae (e.g. Rubivirus). Viruses falling within these families can cause a variety of diseases or symptoms, including, but not limited to: arthritis, bronchiollitis, encephalitis, eye infections (e.g. conjunctivitis, keratitis), chronic fatigue syndrome, hepatitis (A, B, C, E, Chronic Active, Delta), meningitis, opportunistic infections (e.g. AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g. Kaposi's, warts), and viremia. A therapeutic composition of the present invention can be used to treat any of these symptoms or diseases.

Similarly, bacterial or fungal agents that can cause disease or symptoms and that can be treated by a therapeutic composition of the present invention include, but are not limited to, the following Gram-Negative and Gram-positive bacterial families and fungi: Actinomycetales (e.g. Corynebacterium, Mycobacterium, Norcardia), Aspergillosis, Bacillaceae (e.g. Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g. Acinetobacter, Gonorrhea, Menigococcal), Pasteurellacea Infections (e.g. Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g. AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g. cellulitis, dermatocycoses), toxemia, urinary tract infections, wound infections. A therapeutic composition of the present invention can be used to treat any of these symptoms or diseases.

Moreover, parasitic agents causing disease or symptoms that can be treated by a therapeutic composition of the present invention include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g. dysentery, giardiasis), liver disease, lung disease, opportunistic infections (e.g. AIDS related), Malaria, pregnancy complications, and toxoplasmosis. A therapeutic composition of the present invention can be used to treat any of these symptoms or diseases.

Regeneration

A therapeutic composition of the present invention can be used to differentiate, proliferate, and attract cells, fostering the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, or systemic cytokine damage.

Therapeutic compositions of the invention may promote the regeneration of a variety of tissues, including but not limited to organs (e.g. pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration incurs a small amount of scarring, or occurs without scarring. Regeneration also may include angiogenesis.

Moreover, a therapeutic composition of the present invention may increase regeneration of tissues difficult to heal. For example, increased tendon/ligament regeneration would quicken recovery time after damage. A therapeutic composition of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a therapeutic composition of the present invention to proliferate and differentiate nerve cells. Diseases that could be treated using this method include central and peripheral nervous system diseases, neuropathies, or mechanical and traumatic disorders (e.g. spinal cord disorders, head trauma, cerebrovascular disease, and stoke).

Specifically, diseases associated with peripheral nerve injuries, peripheral neuropathy (e.g. resulting from chemotherapy or other medical therapies), localized neuropathies, and central nervous system diseases (e.g. Alzheimer's disease, Parkinson's disease, Huntington's disease, amyotrophic lateral sclerosis, and Shy-Drager syndrome), could all be treated using therapeutic compositions of the present invention. With respect to CNS disorders, numerous means are known in the art for facilitating therapeutic access to brain tissue, including methods for disrupting the blood brain barrier, and methods of coupling therapeutic agents to moieties that provide for transport into the CNS. In one embodiment, a therapeutic nucleic acid is engineered so as to encode a fusion protein, which fusion protein comprises a transport moiety and a therapeutic protein. Alternatively, the subject compositions may be delivered directly to the CNS.

Chemotaxis

In one embodiment, a therapeutic composition of the invention can modulate chemotaxis. For example, in one embodiment, a therapeutic polypeptide of the present invention possesses a chemotaxis activity. A chemotaxic molecule attracts or mobilizes cells (e.g. monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

For example, a therapeutic polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a therapeutic composition of the present invention may inhibit chemotactic activity. These therapeutic compositions could also be used to treat disorders. Thus, a therapeutic composition of the present invention could be used as an inhibitor of chemotaxis.

Especially preferred for use are protherapeutic proteins that are activated in the vicinity of target tissues.

Additional therapeutic polypeptides contemplated for use include, but are not limited to, growth factors (e.g., growth hormone, insulin-like growth factor-1, platelet-derived growth factor, epidermal growth factor, acidic and basic fibroblast growth factors, transforming growth factor-β, etc.), to treat growth disorders or wasting syndromes; and antibodies (e.g., human or humanized), to provide passive immunization or protection of a subject against foreign antigens or pathogens (e.g., H. Pylori), or to provide treatment of cancer, arthritis or cardiovascular disease; cytokines, interferons (e.g., interferon (IFN), IFN-α2b and 2α, IFN-αN1, IFN-β1b, IFN-gamma), interleukins (e.g., IL-1 to IL-10), tumor necrosis factor (TNF-α TNF-β), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (tPA), urokinase, streptokinase, phenylalanine ammonia lyase, brain-derived neurotrophic factor (BDNF), nerve growth factor (NGF), thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin, parathyroid hormone (PTH)-like hormone, soluble CD4, and antibodies and/or antigen-binding fragments (e.g, FAbs) thereof (e.g., orthoclone OKT-e (anti-CD3), GPIIb/IIa monoclonal antibody). Additionally contemplated are therapeutic RNAs targeting nucleic acids encoding such factors.

Vaccine

In one embodiment, the invention provides methods for vaccinating a patient. The methods comprise administering a composition of the invention capable of producing the desired epitope. In a preferred embodiment, the composition comprises a therapeutic nucleic acid construct capable of expressing a protein comprising the epitope.

Cosmetic Applications

In one embodiment, the invention provides DD-chitosan nucleic acid polyplexes for cosmetic use. The subject cosmetics comprise DD-chitosan nucleic acid polyplexes in a formulation suitable for cosmetic use.

EXAMPLES

Formation of dually derivatized chitosan and formation of DNA polyplexes

Chitosan was dually derivatized with arginine and gluconic acid (DD-chitosan) according to well-known methods. DD-chitosan was polyplexed with either a DNA vector encoding for secreted alkaline phosphatase (SEAP) or luciferase siRNA.

In Vitro Transfection with DNA Polyplex

In general, in vitro transfection of 293T cells with DD-chitosan nucleic acid polyplex formulations was performed in two steps: preparation of cells followed by transfection.

Maintenance of Cell Lines

The 293T cell line was courtesy of Dr. Kieffer's lab at UBC and were prepared as follows. Human kidney cells were transformed with the SV40 T-antigen; grown in high glucose Dulbecco's Modified Eagle Medium (DMEM) containing 10% fetal bovine serum (FBS) and penicillin/streptomycin; and maintained below 80% confluency. HT1080 (epithelial cells from human connective tissue) and HeLa (human cervical epithelial cells) are grown in MEM (minimum essential media) containing 10% FBS and penicillin/streptomycin; and maintained below 90% confluency. VERO (monkey kidney epithelial cells) are grown in DMEM containing 10% heat inactivated FBS (56° C. for 30 min), 1 mM sodium pyruvate and 500 ug/ml gentamicin; and maintained below 90% confluency. NIH3T3 (mouse embryonic fibroblasts) are grown in DMEM containing 10% FBS and penicillin/streptomycin; and maintained below 90% confluency.

Preparation of Cells for Transfection

Cells were prepared for transfection as follows. On the day before transfection, 293T cells were added to 6-well tissue culture plates ($4.5 \times 10^5$ cells/well) in 3 mL of complete media (high glucose DMEM+10% FBS+pen/strep). On the day of transfection, cell count was determined for two selected wells by washing cells 1× with phosphate buffered saline (PBS) trypsinizing cells with 0.5 mL of 0.05% trypsin, adding 0.5 mL of complete media and counting 10 μL using a hemocytometer. If cells were ~50% confluent (~$7 \times 10^5$ cells/well), then transfection proceeded. (If cells were too sparse or too confluent, then transfection did not proceed.) Similarly, on the day before transfection, HeLa cells were plated at 1×10$^5$ cells/well, while HT1080, NIH3T3 and VERO cells were plated at 2×10$^5$ cells/well in 3 ml of their respective complete media and transfection was done the next day at ~50% confluency.

Transfection of Cells

Transfection was carried out as follows. First, media was removed from each well followed by addition of 1 mL Opti-mem (pH 7.4) to each well, swirling gently and then removal. (Six wells were washed at a time to prevent cells from dislodging.) Then another 1 mL of Opti-mem (pH 7.4) was added carefully to each well so as not to dislodge cells. Next, polyplex samples were added to each well (target of 2 μg DNA), swirled and incubated at 37° C. for 2 h. After incubation, the media was removed and replaced with 2 mL of complete media and re-incubated at 37° C. At the required time points, the supernatant was removed and stored at −20° C. for subsequent SEAP assay.

SEAP Protein Assay

The SEAP assay was performed using the SEAP Chemiluminescent Assay kit. All reagents for the assay were equilibrated at 25° C. for 30 min before use. Standards for the assay were prepared by dissolving placental alkaline phosphatase to 1 mg/mL in 1× dilution buffer from the kit spiked with 0.1% bovine serum albumin and 50% glycerol and then diluting by 10-fold serial dilutions with DMEM to 0.01 pg/uL. Standards and thawed samples were then diluted 1 in 4 with dilution buffer, heat inactivated at 65° C. for 30 min, incubated on ice for 2 min, centrifuged (16100×rcf for 2 min at RT) and the supernatants transferred to new tubes. After equilibrating at 25° C. for 5 min, 50 uL of the samples and standards were added to each well of a Microlite-1 plate in duplicate. Inactivation buffer (50 uL) was then added to each well and pipetted up and down gently to mix, without creating bubbles and incubated for 5 min. The substrate/enhancer reagent was prepared during the 5 min incubation at a ratio for 1:19 of substrate to enhancer. The substrate/enhancer was then added to each well, incubated for 20 min and then the plate was read in the luminometer (Lmax11384, Molecular Devices) with an integration time of 1 sec.

SEAP mRNA Assay—Quantitative-Real Time-Polymerase Chain Reaction (Q-RT-PCR)

Relative quantification of SEAP mRNA expression in various samples were determined by Q-RT-PCR. Briefly, total mRNA was extracted and purified using TRIzol Reagent and Q-RT-PCR was done using Superscript II. SEAP gene primers and fluorigenic probe were designed using Primer Express (Version 1.5) (Applied Biosystems, Foster City, Calif.). The ABI 7000 sequence detection system (Applied Biosystems) was used to perform all polymerase chain reactions (PCR) in a total volume of 25 Each reaction mixture contained 1×TaqMan Universal Master Mix, 20 μM of each primer and 10 μM of probe. Ten microliters of each complementary DNA (equivalent to 4.5-45 ng of reverse transcribed total RNA) was used in each PCR reaction. The PCR process consisted of an initial incubation at 50° C. for 2 min, followed by a 10-min incubation at 95° C., 40 cycles of PCR at 95° C. for 15 seconds and 1 minute at 60° C. Each 96-well assay plate contained minus reverse transcriptase and minus complementary DNA controls. The results were normalized to housekeeping gene GAPDH (reference gene) and expressed as the relative target gene expression ratio between the treated tissue and the untreated control tissue. The method is referred to as Pfaffl's method (Pfaffl M W. Nucleic Acids Res (2001) 29:e45)

siRNA Knockdown Transfection of Cells

Knockdown of gene expression was carried out by first transfecting host cells with siRNA/modified-dd-chitosan polyplexes followed by transfecting the same host cells with DNA/Lipofectamine 2000.

On the day before transfection, 9×10$^4$ 293T cells/well of a 24-well plate in 1 ml of complete media was plated. On the day of transfection, cells (50% confluent) were washed Opti-mem prior to transfection. Cells were washed by removing media in the well, adding back 0.25 ml of Opti-mem, swirling in place followed by removing the Opti-mem and replacing with 0.25 ml of fresh Opti-mem. siRNA transfection was carried out by adding 200 nM of siRNA/modified-chitosan polyplex to each well and incubating at 37 C in a 5% $CO_2$ incubator. After 2 h, the Opti-mem was removed and replaced with 0.5 ml of complete media. DNA transfection was carried out by adding 0.4 ug of Luciferase-containing Lipofectamine particles to each well and incubating to 37 C in a 5% $CO_2$ incubator. After 2 h, the media was removed and replaced with 0.5 ml fresh complete media, and then the cells were returned to the incubator. Forty-eight hours after transfection with siRNA, cell lysate were collected for luciferase assay. For collection, cells were washed with Dulbecco's phosphate buffered saline, and spiked with 500 ul of Glo Lysis Buffer, containing EDTA-free protease inhibitors, collected to tubes after 5 min incubation and assayed immediately or stored at −80° C.

Luciferase Assay

The luciferase assay was performed using the Bright-Glo Luciferase Assay System. Glo Lysis Buffer, Bright-Glo Buffer and samples for the assay were equilibrated to room temperature before use. Standards for the assay were prepared by diluting QuantiLum Recombinant Luciferase enzyme in 1× Glo Lysis Buffer containing EDTA-free protease inhibitor and 1 mg/ml BSA to 90 ng/ml, then to 30 ng/ml and then diluting by 10-fold serial dilutions to 0.003 ng/ml. Bright-Glo Substrate was reconstituted with Bright-Glo Buffer to make the Bright-Glo Assay Reagent for at least 10 min before use. One hundred uL of the samples and standards were added to each well of a Microlite-1 plate in duplicate. Bright-Glo Assay Reagent (100 uL) was then added to each well and incubated for 2 min in the luminometer and read with an integration time of 1 sec.

Animals

The surgical protocols for the animal studies were approved by the University of British Columbia Committee for Animal Care. The animal work was conducted by qualified and trained staff, Female ~8 weeks old C57BL/6 mice were purchased from Jackson Laboratory (Bar Harbour, Me.). Mice were housed 2-4 animals per cage in a 12 h light/dark cycle and given one week to acclimatize, as well as standard rodent chow (Research Diets Inc., New Brunswick, N.J.) and water ad libitum. Mice were housed at an animal facility in the Department of Physiology, University of British Columbia (UBC).

Colon Transfection in Mice

Naïve C57BL/6 mice were anesthetized (1.5-2.0% isoflurane inhalant, Baxter CA2L9108) and given a single enema delivery of functionalized DD-chitosan-DNA polyplex or non-functionalized-chitosan-DNA polyplex carrying gWiz-SEAP plasmid at 0.25 mg/mL. After 2 days, mice were sacrificed and tissues were harvested.

In Vivo Mouse Transfection: Polyplex Delivery to Muscle

For delivery of marker to mouse muscle, the DD-chitosan-DNA polyplex comprising SEAP expression vector is administered by injection into the medial hamstring. Mice are anesthetized and 50 uL of polyplex is injected via syringe. At various time points, mice are sacrificed and their muscle tissues collected and processed for mRNA expression of SEAP. DNA is injected alone as control.

Lyophilization and reconstitution of DD-chitosan-nucleic acid polyplexes with water DD-chitosan-nucleic acid polyplexes frozen at −80° C. (280 ul each) were placed in a pre-cooled vessel. The vessel was then connected to a lyophilizer (SAVANT-Modulyo D). The polyplexs were freeze-dry under constant pressure of 5 torr at temperature <−40° C. for more than 28 hours. Following lyophilization, the DD-chitosan-nucleic acid polyplexes was reconstituted with water to the original concentration for subsequent experiments.

Results

Figure 3:
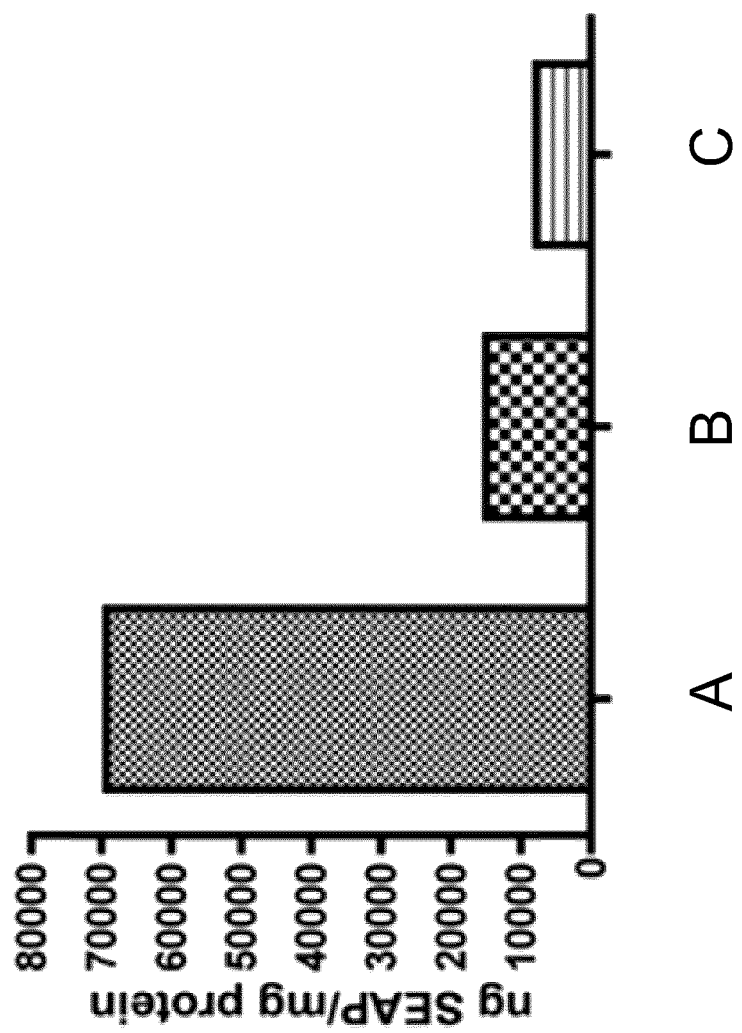
FIG. 3 shows the transfection efficiency (ng SEAP/mg protein; y-axis) of polyplexes made at an amine/phosphate (N/P) ratio of 20 with 24mer chitosan that was (A) dually coupled with arginine and gluconic acid to final functionalization degrees of 26% arginine and 5% gluconic acid; (B) coupled with arginine alone to final functionalization degree of 26%, or (C) coupled with gluconic acid alone at an initial concentration of 30% gluconic acid to total amine.
Figure 4:
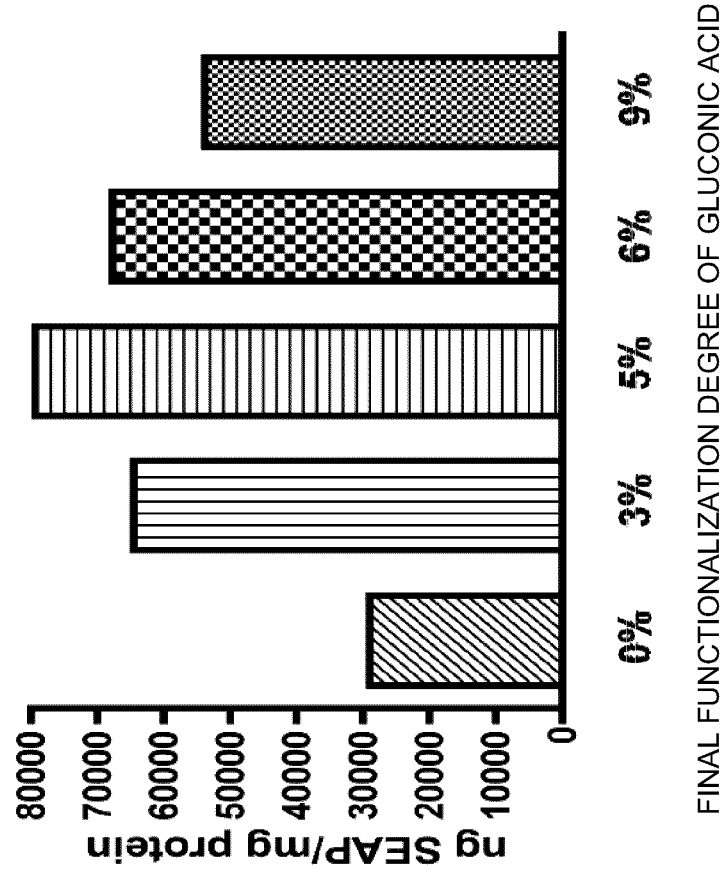
FIG. 4 shows the transfection efficiency (ng SEAP/mg protein; y-axis) of polyplexes made at an amine/phosphate (N/P) ratio of 20 with 24mer chitosan coupled with final functionalization of 26% arginine alone (0%; x-axis) or further coupled with gluconic acid to final functionalization degrees of gluconic acid of 3%, 5%, 6% and 9% (x-axis).
Figure 5:
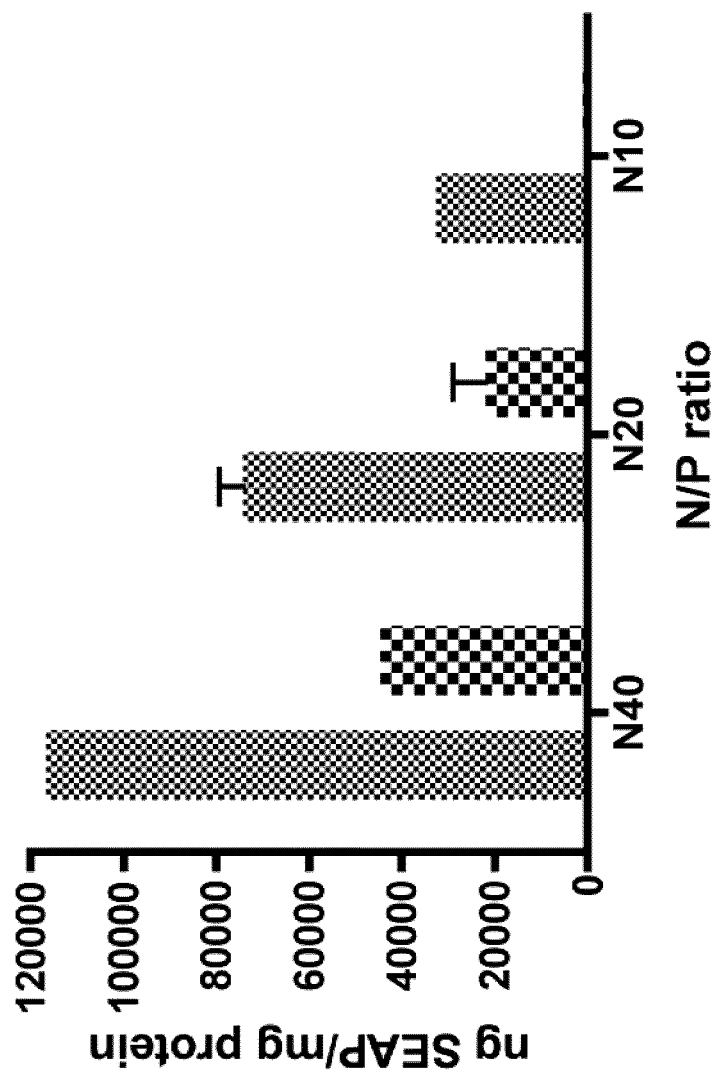
FIG. 5 shows the effect of an amine/phosphate (N/P) ratio (x-axis) of 40 (N40), 20 (N20) or 10 (N10) on the transfection efficiency (ng SEAP/mg/protein; y-axis) of 24mer chitosan dually derivatized with arginine and gluconic acid at final functionalization degrees of 26% and 5%, respectively (small checkered boxes) or chitosan coupled with 26% arginine alone (large checkered boxes).
Figure 6:
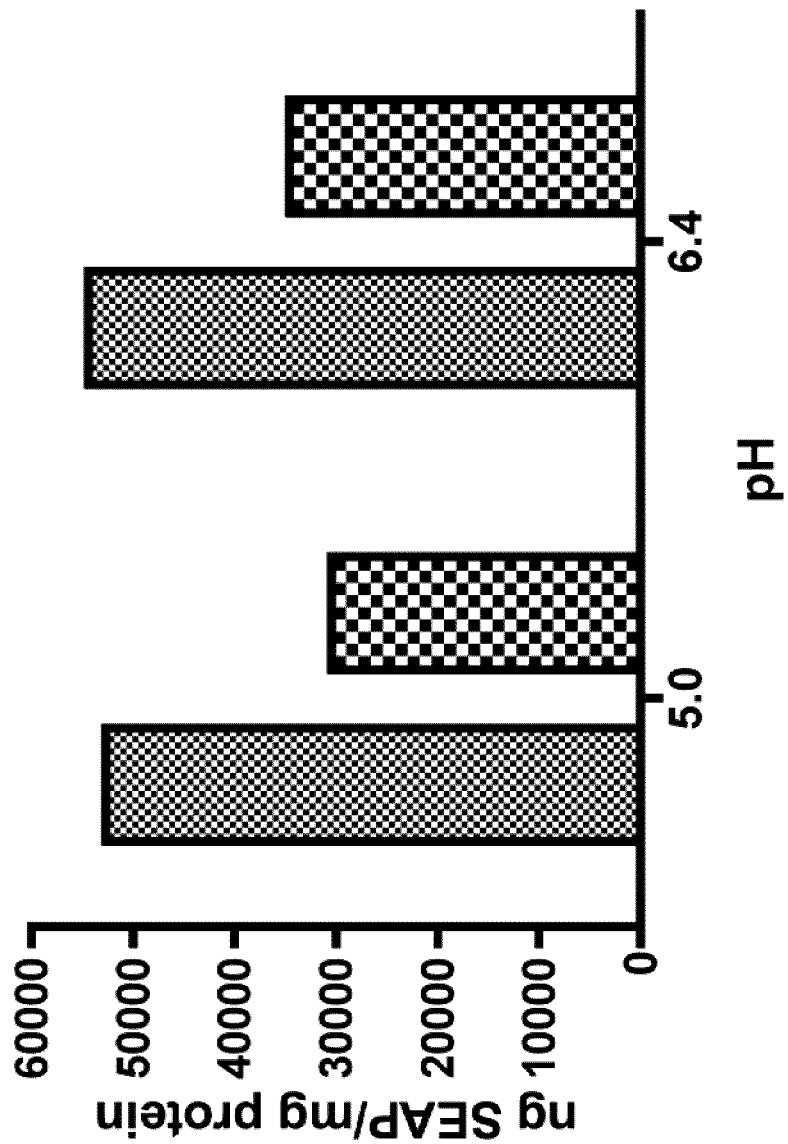
FIG. 6 shows the effect of pH of the formulation (x-axis) on the transfection efficiency (ng SEAP/mg protein) of 24mer chitosan dually derivatized with arginine and gluconic acid at final functionalization degrees of 26% and 5%, respectively (small checkered boxes) or chitosan coupled with arginine only at a final functionalization degree of 26% (large checkered boxes).
Figure 7:
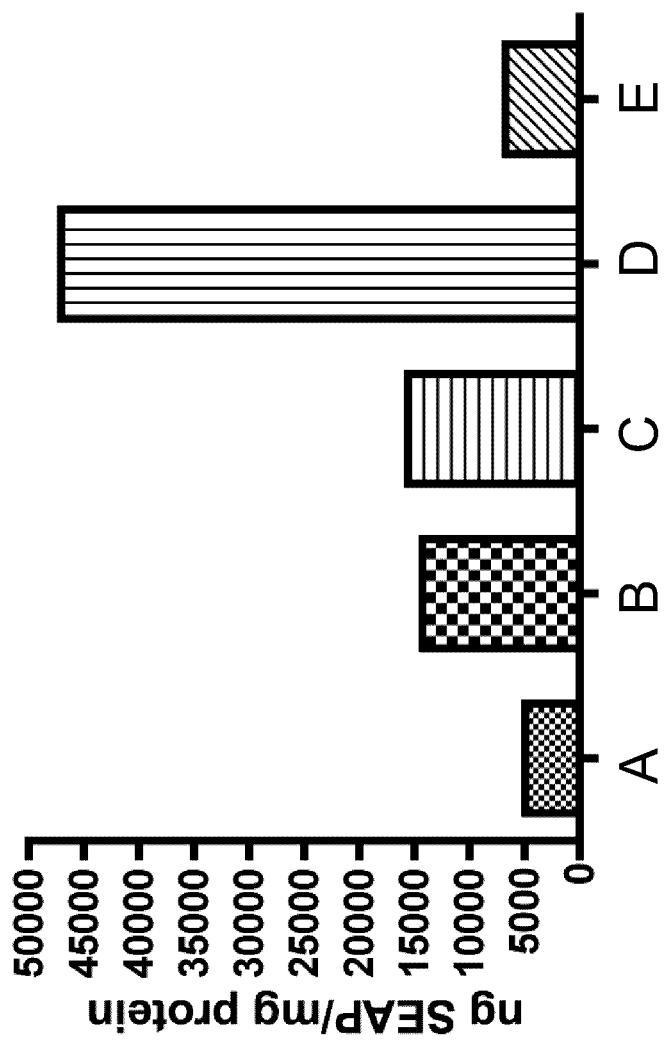
FIG. 7 shows the effect of percent arginine functionalization on transfection efficiency (ng SEAP/mg/protein; y-axis) by 24mer chitosan derivatized with arginine at a final concentration of 52% (A, B) or 26% (C, D) alone (A, C) or also with gluconic acid at a final concentration of 8% (B) or 6% (D). 24mer chitosan coupled with 30% initial concentration gluconic acid alone (E) is also included as a reference.
Figure 8A:
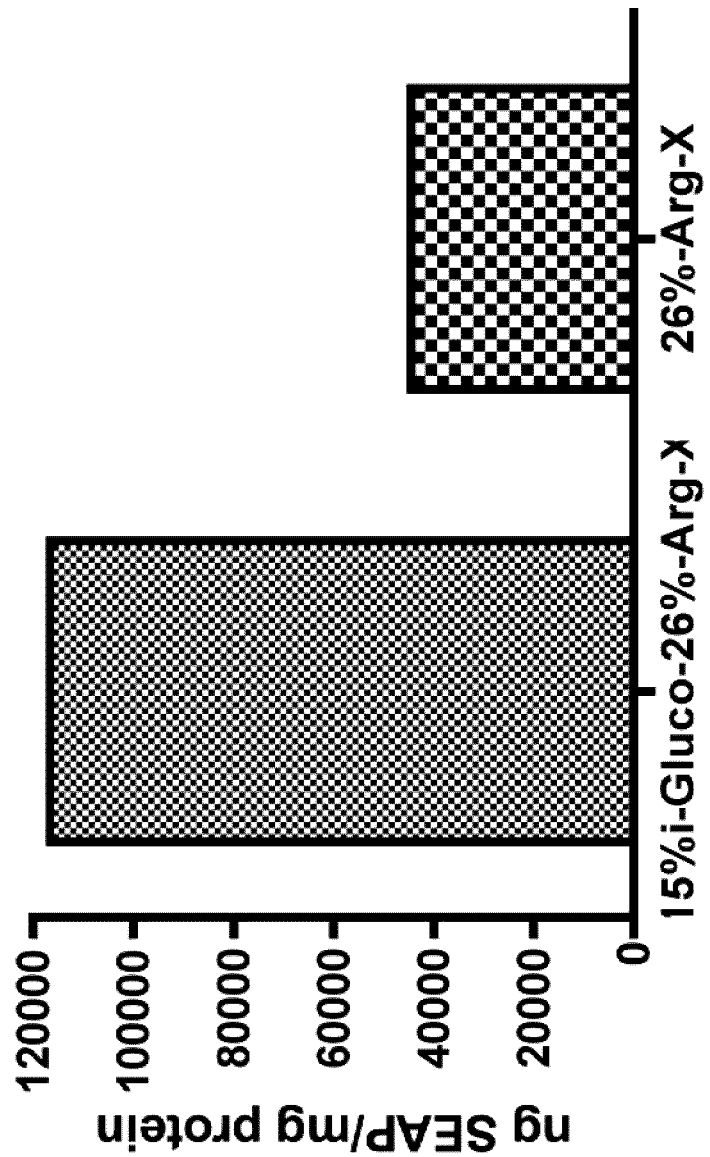
FIG. 8 shows the transfection efficiency of 24mer chitosan dually derivatized with arginine and gluconic acid at final functionalization degrees of 26% and 5%, respectively (small checkered boxes) or chitosan coupled with 26% arginine alone (large checkered boxes) in (A) 293T cells, (B) HT1080 or Hela human cell lines or (C) monkey VERO or murine NIH3T3 cell lines.
Figure 8B:
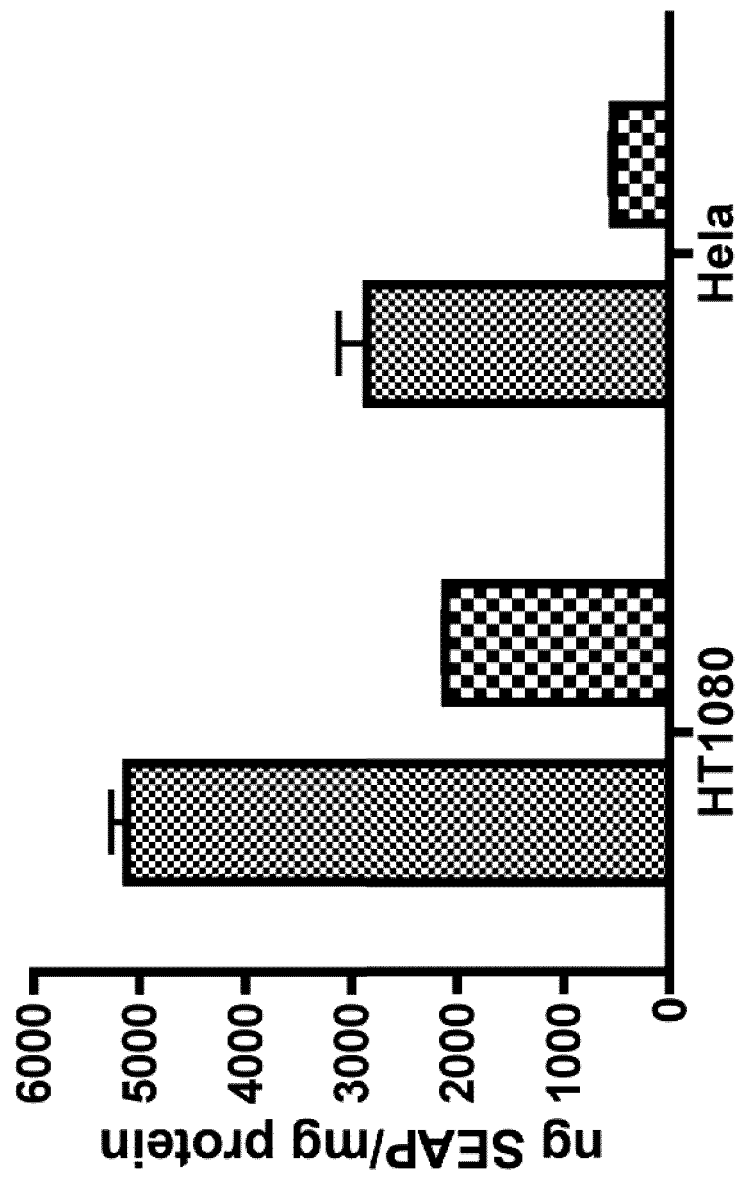
Figure 8C:
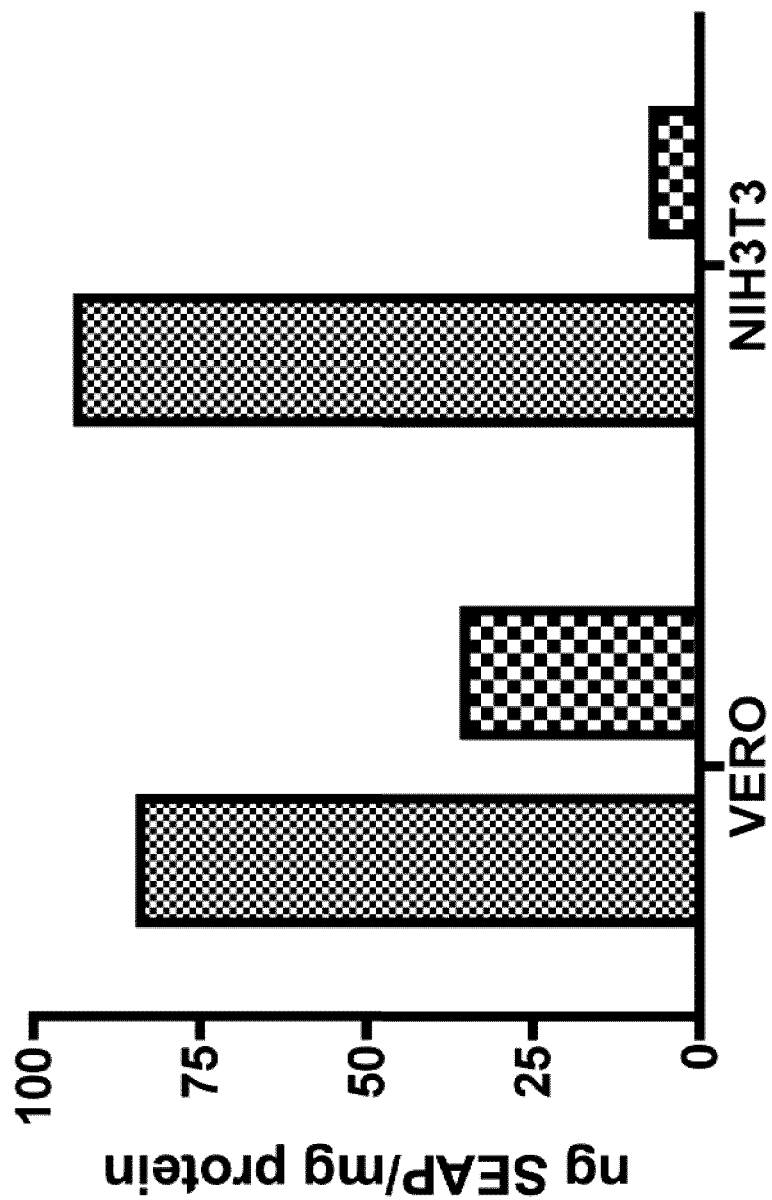
Figure 9:
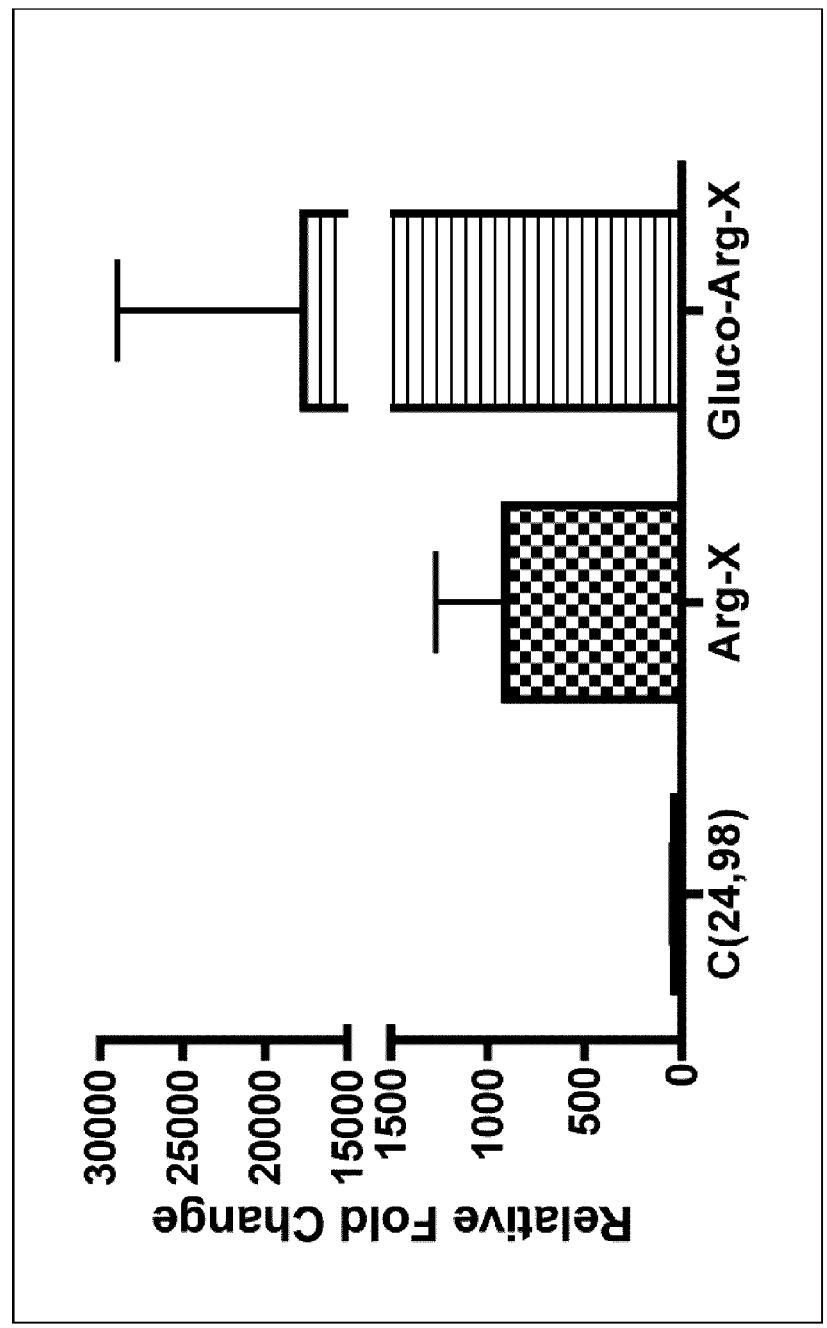
FIG. 9 shows gene expression in muscle 2 days following intramuscular injection of chitosan (A), chitosan functionalized with 26% arginine (B), and chitosan dually functionalized with final functionalization degrees of 26% arginine and 5% gluconic acid (C).
Figure 10:
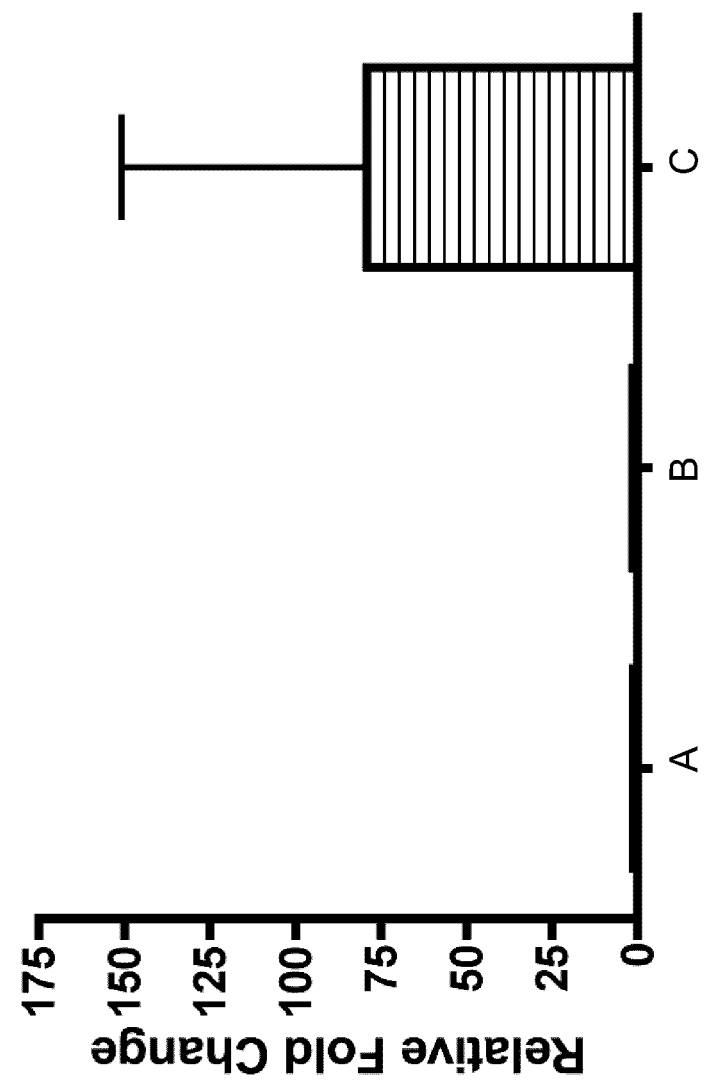
FIG. 10 shows gene expression in distal colon 2 days following colonic delivery of chitosan (A), chitosan functionalized with 26% arginine (B), and chitosan dually functionalized with arginine and gluconic acid at final functionalization degrees of 26% arginine and 6% gluconic acid (C).
Figure 11:
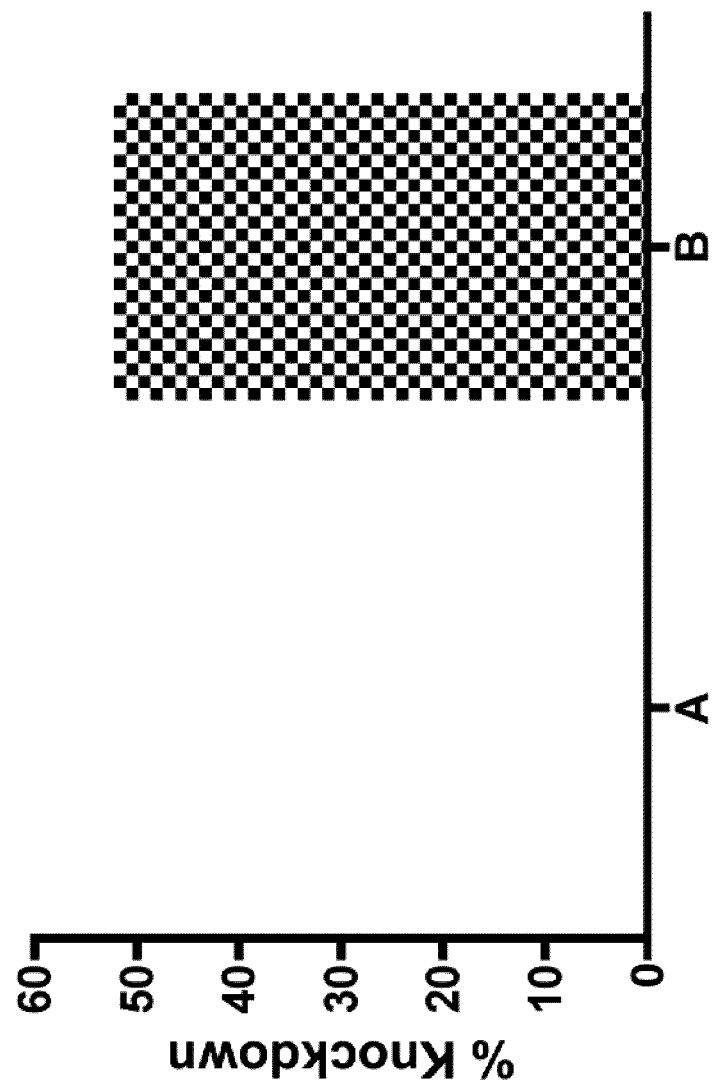
FIG. 11 shows in vitro knock down efficiency of luciferase siRNA polyplexes comprising 24mer chitosan produced at an amine/phosphate (N/P) ratio of 40 and coupled with (A) 26% arginine alone or (B) dually derivatized with 26% arginine and gluconic acid at a final functionalization degree of 5%.

FIGS. 2-4, and 7 show the transfection efficiencies of chitosan derivatized with gluconic acid only (FIG. 2A), arginine only (FIG. 2B) or chitosan dually derivatized with both gluconic acid and arginine in comparison with chitosan derivatized with only arginine or gluconic acid (FIGS. 3 and 7). FIGS. 3 and 7 show a synergistic effect when chitosan is dually derivatized with both arginine and gluconic acid. The synergistic effect may be seen when chitosan is dually functionalized with arginine at a final functionalization degree of 26% and gluconic acid at final functionalization degrees ranging from 3% to 9%, although the greatest effect was seen at a gluconic acid final functionalization degree of about 5% (FIG. 4; see also FIG. 7 showing a synergistic effect with chitosan dually functionalized with arginine and gluconic acid at final functionalization degrees of 26% and 6%, respectively). FIGS. 5 and 6 show the effect of N/P ratio and pH of polyplex formulation, respectively, on transfection efficiency. Transfection efficiencies of both chitosan derivatized with (1) arginine only or (2) arginine and gluconic were directly correlated with N/P ratio, although dually derivatized chitosan had a higher transfection efficiency than chitosan derivatized with arginine alone at all N/P ratios tested (FIG. 5). In contrast, pH did not affect transfection efficiency (FIG. 6). The synergistic effect may also be seen across different cell lines ex vivo (FIG. 8), for siRNA (FIG. 11) and in vivo (FIGS. 9-10). Intramuscular delivery of DD-chitosan-DNA polyplex results in significantly increased SEAP mRNA expression in muscle cells in vivo (FIG. 9). Additionally, relative increases in SEAP mRNA in colon tissue of the treated mice over naïve mice (non-transfected) are shown (FIG. 10). Both frozen and lyophilized DD-chitosan-nucleic acid polyplexes showed stability in physicochemical properties after storage at room temperature for 3 months. These polyplexes also maintained their stability after over-night incubation followed reconstitution with water (FIG. 12).

All citations are expressly incorporated herein in their entirety by reference.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A chitosan-derivative nanoparticle comprising chitosan coupled with gluconic acid and arginine.

2. The nanoparticle according to claim 1, wherein said nanoparticle comprises gluconic acid at an initial concentration of about 5% to about 60%.

3. The nanoparticle according to claim 2, wherein said nanoparticle comprises gluconic acid at an initial concentration of about 8% to about 30%.

4. The nanoparticle according to claim 3, wherein said nanoparticle comprises gluconic acid at a final functionalization of about 3% to about 10%.

5. The nanoparticle according to claim 4, wherein said nanoparticle comprises gluconic acid at a final functionalization of about 5%.

6. The nanoparticle according to claim 1, wherein said nanoparticle comprises arginine at a concentration of about 10% to about 55%.

7. A dually derivatized (DD) chitosan nucleic acid polyplex comprising the nanoparticle according to any one of claims 1-6.

8. The DD-chitosan nucleic acid polyplex according to claim 7, wherein said nucleic acid is DNA or RNA.

9. The DD-chitosan nucleic acid polyplex according to claim 7, wherein the amine to phosphate ratio of said DD-chitosan nucleic acid polyplex is between 2 to 100.

10. The DD-chitosan nucleic acid polyplex according to claim 9, wherein said amine to phosphate ratio of said DD-chitosan nucleic acid polyplex is between 2 to 50.

11. The DD-chitosan nucleic acid polyplex according to claim 10, wherein said amine to phosphate ratio of said DD-chitosan nucleic acid polyplex is between 2 to 30.

12. The DD-chitosan nucleic acid polyplex according to claim 11, wherein said amine to phosphate ratio of said DD-chitosan nucleic acid polyplex is between 2 to 15.

13. A method of delivering a nucleic acid molecule to a cell comprising contacting said cell with a DD-chitosan nucleic acid polyplex according to claim 7.

14. The method of claim 13, wherein said cell is in vivo.

15. The DD-chitosan nucleic acid polyplex according to claim 7, wherein said DD-chitosan nucleic acid polyplex has a combined degree of functionalization with said arginine and said gluconic acid of 1-60%.

16. The DD-chitosan nucleic acid polyplex according to claim 7, wherein said DD-chitosan nucleic acid polyplex has a combined degree of functionalization with said arginine and said gluconic acid of 1-30%.

17. The DD-chitosan nucleic acid polyplex according to claim 7, wherein said nucleic acid is selected from the group consisting of peptide nucleic acid (PNA), phosphorodiamidate morpholino oligo (PMO), locked nucleic acid (LNA), glycol nucleic acid (GNA), and threose nucleic acid (TNA).

18. The DD-chitosan nucleic acid polyplex according to claim 8, wherein said RNA is selected from the group consisting of antisense RNA, siRNA, short hairpin RNA, micro RNA, and enzymatic RNA.

19. The DD-chitosan nucleic acid polyplex according to claim 7, wherein said chitosan molecules have an average molecular weight of less than 110 kDa.

20. The DD-chitosan nucleic acid polyplex according to claim 7, wherein said DD-chitosan nucleic acid polyplex has an average polydispersity index (PDI) selected from the group consisting of less than 0.5, less than 0.4, less than 0.3, and less than 0.25.

21. The DD-chitosan nucleic acid polyplex according to claim 7, wherein said DD-chitosan nucleic acid polyplex has a molar ratio of said arginine to said gluconic acid of between 100:1 and 1:100.

22. The DD-chitosan nucleic acid polyplex according to claim 21, wherein said molar ratio of said arginine to said gluconic acid is between 50:1 and 1:50.

23. The DD-chitosan nucleic acid polyplex according to claim 21, wherein said molar ratio of said arginine to said gluconic acid is between 10:1 and 1:10.

24. The DD-chitosan nucleic acid polyplex according to claim 21, wherein said molar ratio of said arginine to said gluconic acid is between 5:1 and 1:5.

25. The DD-chitosan nucleic acid polyplex according to claim 21, wherein said molar ratio of said arginine to said gluconic acid is between 2:1 and 1:2.

26. A pharmaceutical composition comprising said DD-chitosan nucleic acid polyplex of claim 7.

\* \* \* \* \*